US005700671A

United States Patent [19]
Prieto et al.

[11] Patent Number: 5,700,671
[45] Date of Patent: Dec. 23, 1997

[54] METHODS OF MAKING TRANSGENIC ANIMALS PRODUCING OLIGOSACCHARIDES AND GLYCOPROTEINS

[75] Inventors: Pedro Antonio Prieto, Columbus, Ohio; David Fletcher Smith, Athens, Ga.; Richard Dale Cummings, Edmond, Okla.; John Joseph Kopchick, Athens; Pradip Mukerji, Gahanna, both of Ohio; Kelley Wilson Moremen; James Michael Pierce, both of Athens, Ga.

[73] Assignee: Abbott Laboratories, Abbott Park, Ill.

[21] Appl. No.: 434,151

[22] Filed: May 2, 1995

Related U.S. Application Data

[62] Division of Ser. No. 209,132, Mar. 9, 1994.

[51] Int. Cl.⁶ .............. C12N 15/00; C12N 9/10; C12Q 1/68; C12P 21/06
[52] U.S. Cl. .......... 435/172.3; 435/6; 435/69.1; 435/193; 800/2
[58] Field of Search ............... 800/2, DIG. 1; 435/172.3, 69.1, 240.2, 320.1; 935/11, 15, 70, 111

[56] References Cited

U.S. PATENT DOCUMENTS

| | | |
|---|---|---|
| 5,032,519 | 7/1991 | Paulson et al. . |
| 5,047,335 | 9/1991 | Paulson et al. . |
| 5,180,674 | 1/1993 | Roth . |
| 5,322,775 | 6/1994 | Clark et al. .............. 435/69.1 |
| 5,565,362 | 10/1996 | Rosen . |

FOREIGN PATENT DOCUMENTS

| | | |
|---|---|---|
| 0279582 | 8/1988 | European Pat. Off. . |
| 8800239 | 1/1988 | WIPO . |
| 8801648 | 3/1988 | WIPO . |
| 9005188 | 5/1990 | WIPO . |
| 9112340 | 8/1991 | WIPO . |
| 9203917 | 3/1992 | WIPO . |
| 9208692 | 5/1992 | WIPO . |
| 9315196 | 8/1993 | WIPO . |
| 9325567 | 12/1993 | WIPO . |
| 9325669 | 12/1993 | WIPO . |

OTHER PUBLICATIONS

J. Van Brunt, "Molecular Farming: Transgenic Animals As Bioreactors", Biotechnology Nature Publishing, vol.: 6, Oct. 1988, pp. 1149–1154.

Yom et al., "Genetic engineering of milk composition: modification of milk components in lactating transgenic animals [1–3]", Am. J Clin. Nutr., 1993:58 (suppl): 299S–306S.

V.P. Rajan, et al., "A Cloned Human DNA Restriction Fragment Determines Expression of a GDP-L-fucose:β-D-Galactoside 2-a-L-fucosyltransferase in Transfected Cells", Journal of Biology Chemistry, vol. 264, No. 19, Issue of Jul. 5, pp. 11158–11167 (1989).

R.D. Larsen, et al., "Molecular cloning, sequence, and expression of a human GDP-L-fucose: β-D-galactoside 2-a-L-fucosyltransferase cDNA that can form the H blood group antigen", Proc. Natl. Acad. Sci. USA, vol. 87, pp. 6674–6678, Sep. 1990.

T. Burdon, et al., "Over-expression of an endogenous milk protein gene in transgenic mice is associated with impaired mammary alveolar development and a milchlos phenotype", Mechanisms of Development, vol.: 36, (1991) 67–74.

C.A. Kappel, et al., "Regulating gene expression in transgenic animals", Current Opinion in Biotechnology 1992, 3:548–553.

A. Shamay, et al., "Expression of the whey acidic protein in transgenic pigs impairs mammary development", Transgenic Research 1, 124–132 (1992).

D.H. Joziasse, "Mammalian glycosyltransferases: genomic organization and protein structure", Glycobiology, vol. 2(4) 271–277 (1992).

R.J. Wall, et al., "High-level synthesis of a heterologous milk protein in the mammary glands of transgenic swine", Pro. Natl. Acad. Sci. USA, vol. 88: pp. 1696–1700, (Mar. 1991).

T. Koch, et al., "Antibody Catalysis of Multistep Reactions: An Aldol Addition Followed by a Disfavored Elimination", Journal of the American Chemical Society, vol. 117, No. 37, pp. 9383–9387, (Sep. 20, 1995).

Primary Examiner—Jasemine C. Chambers
Assistant Examiner—Deborah Crouch
Attorney, Agent, or Firm—Cheryl L. Becker

[57] ABSTRACT

The invention relates to transgenic non-human mammals characterized in that the genome of said mammals contain at least one heterologous gene encoding for the production of heterologous catalytic entity selected from the group consisting of enzymes and antibodies, and wherein said catalytic entity produces a second heterologous product in the milk of said mammal. Especially useful in the practice of the invention are human glycosyltransferases and transgenic sheep, goats and cows. The heterologous product includes oligosaccharides and glycoconjugates.

8 Claims, 15 Drawing Sheets

```
            10         20         30         40         50
             *          *          *          *          *
        GAATTCGGCTTATCTGCCACCTGCAAGCAGCTCGGCC ATG TGG CTC CGG AGC
        CTTAAGCCGAATAGACGGTGGACGTTCGTCGAGCCGG TAC ACC GAG GCC TCG
                                              Met Trp Leu Arg Ser>
                                              ___TRANSLATION_____>

60         70         80         90
             *          *          *          *
        CAT CGT CAG CTC TGC CTG GCC TTC CTG CTA GTC TGT GTC CTC TCT
        GTA GCA GTC GAG ACG GAC CGG AAG GAC GAT CAG ACA CAG GAG AGA
        His Arg Gln Leu Cys Leu Ala Phe Leu Leu Val Cys Val Leu Ser>
        ___a___a___TRANSLATION OF 12 FUC TRANS SEQ (WT)____a___a___>

100        110        120        130        140
             *          *          *          *          *
        GTA ATC TTC TTC CTC CAT ATC CAT CAA GAC AGC TTT CCA CAT GGC
        CAT TAG AAG AAG GAG GTA TAG GTA GTT CTG TCG AAA GGT GTA CCG
        Val Ile Phe Phe Leu His Ile His Gln Asp Ser Phe Pro His Gly>
        ___a___a___TRANSLATION OF 12 FUC TRANS SEQ (WT)____a___a___>

150        160        170        180
             *          *          *          *
        CTA GGC CTG TCG ATC CTG TGT CCA GAC CGC CGC CTG GTG ACA CCC
        GAT CCG GAC AGC TAG GAC ACA GGT CTG GCG GCG GAC CAC TGT GGG
        Leu Gly Leu Ser Ile Leu Cys Pro Asp Arg Arg Leu Val Thr Pro>
        ___a___a___TRANSLATION OF 12 FUC TRANS SEQ (WT)____a___a___>

190        200        210        220        230
             *          *          *          *          *
        CCA GTG GCC ATC TTC TGC CTG CCG GGT ACT GCG ATG GGC CCC AAC
        GGT CAC CGG TAG AAG ACG GAC GGC CCA TGA CGC TAC CCG GGG TTG
        Pro Val Ala Ile Phe Cys Leu Pro Gly Thr Ala Met Gly Pro Asn>
        ___a___a___TRANSLATION OF 12 FUC TRANS SEQ (WT)____a___a___>

240        250        260        270
             *          *          *          *
        GCC TCC TCT TCC TGT CCC CAG CAC CCT GCT TCC CTC TCC GGC ACC
        CGG AGG AGA AGG ACA GGG GTC GTG GGA CGA AGG GAG AGG CCG TGG
        Ala Ser Ser Ser Cys Pro Gln His Pro Ala Ser Leu Ser Gly Thr>
        ___a___a___TRANSLATION OF 12 FUC TRANS SEQ (WT)____a___a___>
```

FIG.1A

```
280         290         300         310         320
 *           *           *           *           *
TGG ACT GTC TAC CCC AAT GGC CGG TTT GGT AAT CAG ATG GGA CAG
ACC TGA CAG ATG GGG TTA CCG GCC AAA CCA TTA GTC TAC CCT GTC
Trp Thr Val Tyr Pro Asn Gly Arg Phe Gly Asn Gln Met Gly Gln>
___a___a___TRANSLATION OF 12 FUC TRANS SEQ (WT)___a___a___>

330         340         350         360
        *           *           *           *
TAT GCC ACG CTG CTG GCT CTG GCC CAG CTC AAC GGC CGC CGG GCC
ATA CGG TGC GAC GAC CGA GAC CGG GTC GAG TTG CCG GCG GCC CGG
Tyr Ala Thr Leu Leu Ala Leu Ala Gln Leu Asn Gly Arg Arg Ala>
___a___a___TRANSLATION OF 12 FUC TRANS SEQ (WT)___a___a___>

370         380         390         400         410
 *           *           *           *           *
TTT ATC CTG CCT GCC ATG CAT GCC GCC CTG GCC CCG GTA TTC CGC
AAA TAG GAC GGA CGG TAC GTA CGG CGG GAC CGG GGC CAT AAG GCG
Phe Ile Leu Pro Ala Met His Ala Ala Leu Ala Pro Val Phe Arg>
___a___a___TRANSLATION OF 12 FUC TRANS SEQ (WT)___a___a___>

420         430         440         450
        *           *           *           *
ATC ACC CTG CCC GTG CTG GCC CCA GAA GTG GAC AGC CGC ACG CCG
TAG TGG GAC GGG CAC GAC CGG GGT CTT CAC CTG TCG GCG TGC GGC
Ile Thr Leu Pro Val Leu Ala Pro Glu Val Asp Ser Arg Thr Pro>
___a___a___TRANSLATION OF 12 FUC TRANS SEQ (WT)___a___a___>

460         470         480         490         500
 *           *           *           *           *
TGG CGG GAG CTG CAG CTT CAC GAC TGG ATG TCG GAG GAG TAC GCG
ACC GCC CTC GAC GTC GAA GTG CTG ACC TAC AGC CTC CTC ATG CGC
Trp Arg Glu Leu Gln Leu His Asp Trp Met Ser Glu Glu Tyr Ala>
___a___a___TRANSLATION OF 12 FUC TRANS SEQ (WT)___a___a___>

510         520         530         540
        *           *           *           *
GAC TTG AGA GAT CCT TTC CTG AAG CTC TCT GGC TTC CCC TGC TCT
CTG AAC TCT CTA GGA AAG GAC TTC GAG AGA CCG AAG GGG ACG AGA
Asp Leu Arg Asp Pro Phe Leu Lys Leu Ser Gly Phe Pro Cys Ser>
___a___a___TRANSLATION OF 12 FUC TRANS SEQ (WT)___a___a___>
```

FIG.1B

```
550         560         570         580         590
 *           *           *           *           *
TGG ACT TTC TTC CAC CAT CTC CGG GAA CAG ATC CGC AGA GAG TTC
ACC TGA AAG AAG GTG GTA GAG GCC CTT GTC TAG GCG TCT CTC AAG
Trp Thr Phe Phe His His Leu Arg Glu Gln Ile Arg Arg Glu Phe>
___a___a___TRANSLATION OF 12 FUC TRANS SEQ (WT)____a___a___>

600         610         620         630
       *           *           *           *
ACC CTG CAC GAC CAC CTT CGG GAA GAG GCG CAG AGT GTG CTG GGT
TGG GAC GTG CTG GTG GAA GCC CTT CTC CGC GTC TCA CAC GAC CCA
Thr Leu His Asp His Leu Arg Glu Glu Ala Gln Ser Val Leu Gly>
___a___a___TRANSLATION OF 12 FUC TRANS SEQ (WT)____a___a___>

640         650         660         670         680
 *           *           *           *           *
CAG CTC CGC CTG GGC CGC ACA GGG GAC CGC CCG CGC ACC TTT GTC
GTC GAG GCG GAC CCG GCG TGT CCC CTG GCG GGC GCG TGG AAA CAG
Gln Leu Arg Leu Gly Arg Thr Gly Asp Arg Pro Arg Thr Phe Val>
___a___a___TRANSLATION OF 12 FUC TRANS SEQ (WT)____a___a___>

690         700         710         720
       *           *           *           *
GGC GTC CAC GTG CGC CGT GGG GAC TAT CTG CAG GTT ATG CCT CAG
CCG CAG GTG CAC GCG GCA CCC CTG ATA GAC GTC CAA TAC GGA GTC
Gly Val His Val Arg Arg Gly Asp Tyr Leu Gln Val Met Pro Gln>
___a___a___TRANSLATION OF 12 FUC TRANS SEQ (WT)____a___a___>

730         740         750         760         770
 *           *           *           *           *
CGC TGG AAG GGT GTG GTG GGC GAC AGC GCC TAC CTC CGG CAG GCC
GCG ACC TTC CCA CAC CAC CCG CTG TCG CGG ATG GAG GCC GTC CGG
Arg Trp Lys Gly Val Val Gly Asp Ser Ala Tyr Leu Arg Gln Ala>
___a___a___TRANSLATION OF 12 FUC TRANS SEQ (WT)____a___a___>

780         790         800         810
       *           *           *           *
ATG GAC TGG TTC CGG GCA CGG CAC GAA GCC CCC GTT TTC GTG GTC
TAC CTG ACC AAG GCC CGT GCC GTG CTT CGG GGG CAA AAG CAC CAG
Met Asp Trp Phe Arg Ala Arg His Glu Ala Pro Val Phe Val Val>
___a___a___TRANSLATION OF 12 FUC TRANS SEQ (WT)____a___a___>
```

FIG.1C

```
       820          830          840          850          860
        *            *            *            *            *
ACC AGC AAC GGC ATG GAG TGG TGT AAA GAA AAC ATC GAC ACC TCC
TGG TCG TTG CCG TAC CTC ACC ACA TTT CTT TTG TAG CTG TGG AGG
Thr Ser Asn Gly Met Glu Trp Cys Lys Glu Asn Ile Asp Thr Ser>
___a___a___TRANSLATION OF 12 FUC TRANS SEQ (WT)____a___a___>

870          880          890          900
        *            *            *            *
CAG GGC GAT GTG ACG TTT GCT GGC GAT GGA CAG GAG GCT ACA CCG
GTC CCG CTA CAC TGC AAA CGA CCG CTA CCT GTC CTC CGA TGT GGC
Gln Gly Asp Val Thr Phe Ala Gly Asp Gly Gln Glu Ala Thr Pro>
___a___a___TRANSLATION OF 12 FUC TRANS SEQ (WT)____a___a___>

910          920          930          940          950
        *            *            *            *            *
TGG AAA GAC TTT GCC CTG CTC ACA CAG TGC AAC CAC ACC ATT ATG
ACC TTT CTG AAA CGG GAC GAG TGT GTC ACG TTG GTG TGG TAA TAC
Trp Lys Asp Phe Ala Leu Leu Thr Gln Cys Asn His Thr Ile Met>
___a___a___TRANSLATION OF 12 FUC TRANS SEQ (WT)____a___a___>

960          970          980          990
        *            *            *            *
ACC ATT GGC ACC TTC GGC TTC TGG GCT GCC TAC CTG GCT GGC GGA
TGG TAA CCG TGG AAG CCG AAG ACC CGA CGG ATG GAC CGA CCG CCT
Thr Ile Gly Thr Phe Gly Phe Trp Ala Ala Tyr Leu Ala Gly Gly>
___a___a___TRANSLATION OF 12 FUC TRANS SEQ (WT)____a___a___>

1000         1010         1020         1030         1040
        *            *            *            *            *
GAC ACT GTC TAC CTG GCC AAC TTC ACC CTG CCA GAC TCT GAG TTC
CTG TGA CAG ATG GAC CGG TTG AAG TGG GAC GGT CTG AGA CTC AAG
Asp Thr Val Tyr Leu Ala Asn Phe Thr Leu Pro Asp Ser Glu Phe>
___a___a___TRANSLATION OF 12 FUC TRANS SEQ (WT)____a___a___>

1050         1060         1070         1080
        *            *            *            *
CTG AAG ATC TTT AAG CCG GAG GCG GCC TTC CTG CCC GAG TGG GTG
GAC TTC TAG AAA TTC GGC CTC CGC CGG AAG GAC GGG CTC ACC CAC
Leu Lys Ile Phe Lys Pro Glu Ala Ala Phe Leu Pro Glu Trp Val>
___a___a___TRANSLATION OF 12 FUC TRANS SEQ (WT)____a___a___>
```

FIG.1D

```
        1090            1100            1110            1120            1130
          *               *               *               *               *
    GGC ATT AAT GCA GAC TTG TCT CCA CTC TGG ACA TTG GCT AAG CCT
    CCG TAA TTA CGT CTG AAC AGA GGT GAG ACC TGT AAC CGA TTC GGA
    Gly Ile Asn Ala Asp Leu Ser Pro Leu Trp Thr Leu Ala Lys Pro>
    ___a___a___TRANSLATION OF 12 FUC TRANS SEQ (WT)____a___a___>

1140            1150
          *               *
    TGA GAGCCAGGGAAGCCGAATTC
    ACT CTCGGTCCCTTCGGCTTAAG
    ***>
    ___>
```

FIG.1E

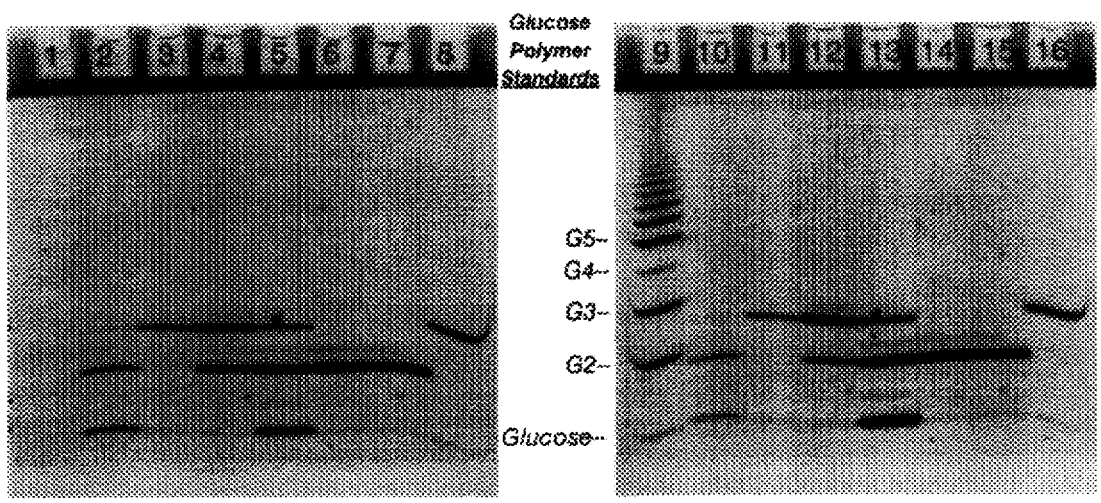

Lane Identification:

1: Tracking Dye
2: 3'Fucosyllactose Standard After Fucosidase
3: 2'Fucosyllactose Standard
4: Pooled Fractions from Mouse 29-119
5: #(4) After Fucosidase Treatment
6: Pooled Fractions from Control Mouse
7: #(6) After Fucosidase Treatment
8: 3'Fucosyllactose Standard After Fucosidase 9: Monosaccharide Standards
10: 2'Fucosyllactose After Fucosidase
11: 2'Fucosyllactose Standard
12: Pooled Fractions from Mouse 28-89
13: #(12) After Fucosidase Treatment
14: Pooled Fractions from Control Mouse
15: #(14) After Fucosidase Treatment
16: 3'Fucosyllactose Standard

FIG. 8

Lane Identification:

1: Monosaccharide composition of 2'fucosyllactose standard
2: Monosaccharide composition of pooled oligosaccharide fractions from transgenic mouse 34-34
3: 3'fucosyllactose
4: Monosaccharide composition of pooled oligosaccharide fractions from transgenic mouse 72-66
5: Monosaccharide standards

METHODS OF MAKING TRANSGENIC ANIMALS PRODUCING OLIGOSACCHARIDES AND GLYCOPROTEINS

This is a Divisional Application of application Ser. No. 08/209,132 filed on Mar. 9, 1994.

TECHNICAL FIELD

This invention relates to the in vivo production of secondary gene products of heterologous glycosyltransferases. These glycosyltransferases are expressed in non-human mammary tissue leading to the production of heterologous oligosaccharides as well as various glycoconjugates bearing those oligosaccharides in the milk of the transgenic animal.

BACKGROUND ART

Carbohydrates are an important class of biological compounds. The term "saccharides" encompasses a wide variety of carbohydrate-containing compounds. These include polysaccharides, oligosaccharides, glycoproteins and glycosides with non-carbohydrate aglycones. Biological macromolecules composed of protein or lipids containing oligosaccharide moieties are collectively known as glycoconjugates. The carbohydrate moiety provides many biological functions.

In cells, carbohydrates function as structural components where they regulate viscosity, store energy, or are key components of the cell surface. The complex oligosaccharide chains of various glycoconjugates (especially glycoproteins and glycolipids) mediate or modulate a variety of biological processes. For a general review of the bioactivity of carbohydrates see: (a) Biology of Carbohydrates, Volume 2, Ginsburg et al, Wiley, New York (1984); and (b) P. W. Macher et al, Annual Review of Biochemistry, Volume 57, page 785, 1988). Among other things, it is known that:

(a) carbohydrate structures are important to the stability, activity, localization and degradation of glycoproteins;

(b) certain oligosaccharide structures activate plant secretion of antimicrobial substances;

(c) glycoconjugates are frequently found on the surfaces of various cells and are important, inter alia, to cell interactions with the surroundings since they function as receptors or regulators when bonded to cell surfaces of, for example, peptides, hormones, toxins, viruses, bacteria and during cell-cell interaction;

(d) carbohydrate structures are antigenic determinants (for example, blood group antigens);

(e) carbohydrates function as cell differentiating antigens during normal tissue development;

(f) carbohydrates are important in oncogenesis since specific oligosaccharides have been found to be cancer-associated antigenic determinants; and (g) oligosaccharides are important to sperm/egg interaction and to fertilization.

Isolated oligosaccharides are known to inhibit the agglutination of uropathogenic coliform bacteria with erythrocytes. Other oligosaccharides have been shown to possess potent antithrombic activity by increasing the levels of plasminogen activator. This same biological activity has been used, by covalently attaching these oligosaccharides to the surface of medical instruments, to produce surfaces which have anticoagulation effects. These surfaces are useful in the collection, processing, storage and use of blood. Still other oligosaccharides have found utility as gram positive antibiotics and disinfectants. Further, certain free oligosaccharides have been used in the diagnosis and identification of specific bacteria. A considerable future market is envisaged for fine chemicals based on biologically active carbohydrates.

Universities and industry are at present working intensely on developing the additional uses of biologically active oligosaccharides. These efforts include, but are not limited to:

(a) the development of novel diagnostics and blood typing reagents;

(b) the development of a novel type of therapy as an alternative to antibiotics, based on the prevention of the adhesion of bacteria and viruses to cell surfaces by means of specific oligosaccharides; and (c) the use of oligosaccharides to stimulate plant growth and provide protection against certain plant pathogens.

A large number of oligosaccharide structures have been identified and characterized. The smallest building block or unit of an oligosaccharide is a monosaccharide. The major monosaccharides found in mammalian glycoconjugates are: D-glucose (Glc), D-galactose (Gal), D-mannose (Man), L-fucose (Fuc), N-acetyl-D-galactose amine (GalNAc), N-acetyl-D-glucose amine (GlcNAc) and N-acetyl-D-neuraminic acid (NeuAc). The abbreviations in parentheses are the standard abridged terminology for monosaccharides according to the recommendations of the International Union of Physics, Chemistry and Biology Council; Journal Biological Chemistry, Volume 257, pages 3347–3354, (1982). These abbreviations will be used hereinafter. Despite the relatively small number of fundamental building blocks, the number of possible combinations is very great because both the anomeric configuration (alpha- or β-glycosidic linkage) as well as the position of the O-glycosidic bond can be varied.

Thus, a large variety of oligosaccharide structures can exist. The bioactivity of oligosaccharides is known to be specific in terms of both sugar conformation and composition. Individual monosaccharides provide one element of bioactivity but they also contribute to the overall conformation of the oligosaccharide thereby providing another level of specificity and bioactivity. It is the diversity of glycoconjugates and oligosaccharides that produces biological specificity of certain oligosaccharide structures. However, this diversity also causes a particular problem for the practical utility of these compounds. Glycoconjugates are typically potent immunogens and the biospecificity, as noted above, is determined not only by the particular monosaccharide sequence but also by the nature of the glycosidic bond. Consequently it is often not possible to use oligosaccharide structures found in one animal species in another species. Similar restrictions on use may also apply on an individual basis. For example, since certain blood group antigens are known to be formed from specific oligosaccharides, it is necessary to be especially careful when conjugating a blood group oligosaccharide to a protein and then using that glycoprotein therapeutically. Careful consideration of the potential immunogenicity concerns must be made.

Despite these potential difficulties, it is well accepted that there is a need to produce large quantities of human oligosaccharides and/or glycoconjugates bearing those oligosaccharides. Numerous methods have been contemplated as suitable means for achieving this goal. Such methods include synthesis of oligosaccharides by conventional organic chemistry or the use of enzymes in vitro. Immobilized enzymes are presently the preferred mode for large scale in vitro oligosaccharide production. This is because of an enzyme's high regio- and stereoselectivity, as well as a high catalytic efficiency under mild reaction conditions. The literature discloses a number of enzyme-catalyzed oligosaccharide syntheses. For example, see the scientific review articles by Y. Ichikawa et al, "Enzyme-catalyzed Oligosaccharide Synthesis" in Analytical Biochemistry, Volume 202, pages 215–238, (1992); and K. G. I. Nillson, "Enzymatic Synthesis of Oligosaccharides" Trends in Biotechnology, Volume 6, pages 256–264, (1988). Both hydrolases and transferases have been used to faciltate production of oligosaccharides. The glycosidase enzymes, a subclass of the hydrolases, are especially useful in the synthesis of oligosaccharides by a process of reversing the degradative cycle. In general, however, enzymatic oligosaccharide synthesis is based on the biosynthetic pathway. While the biosynthetic pathway of oligosaccharide synthesis is principally regulated by the gene encoding the production of each glycosyltransferase, the actual oligosaccharide structures are determined by the substrate and acceptor specificity of the individual glycosyltransferases. Oligosaccharides are synthesized by transferring monosaccharides from sugar nucleotide donors to acceptor molecules. These acceptor molecules may be other free oligosaccharides, monosaccharides, or oligosaccharides bound to proteins or lipids.

Enzymatic oligosaccharide synthesis has generally been conducted only on a small scale because the enzymes, particularly the glycosyltransferases from natural sources, have been difficult to isolate. Also, the sugar nucleotide donors are very difficult to obtain from natural sources and are very expensive when derived from organic chemistry synthesis. More recently however, a recycling and reutilization strategy has been developed for synthesizing large quantities of oligosaccharides. U.S. Pat. No. 5, 180, 674, incorporated herein by reference, discloses a novel affinity chromatography method in which the reaction products are repetitively recycled over the matrix or resin bound glycosyltransferases. Furthermore, recent progress in gene cloning techniques have made several glycosyltransferases available in sufficient quality and quantity to make enzymatic synthesis of oligosaccharides more practical.

The literature is replete with descriptions of recombinant or transgenic expression of a heterologous glycosyltransferase. However, before continuing a discussion of the literature, it is necessary to clarify the meaning of various terms as used herein and in the claims:

(a) Host, host cell or host animal: These terms are used to refer to the cell or mammal which is responsible for the biosynthesis of biological material.

(b) Homologous: This word means that the entity thus characterized is normally present or produced by the host.

(c) Heterologous: This word means that the entity thus characterized is not normally present or produced by the host. In other words, the entity thus characterized is foreign to the host.

(d) Catalytic activity: This term is used to refer to the inherent property of certain biological compounds to facilitate chemical change in other substances.

(e) Catalytic entity: This term is used to refer to biological compounds which inherently possess catalytic activity which results in the production of new, different or altered compounds. Examples hereof are enzymes and antibodies. An enzyme is a biochemical catalyst of a specific biochemical reaction. An enzyme product is formed as a result of the enzyme's catalytic activity on a substrate material.

(f) Genome: This word is used to refer to the complete genetic material found in the host. This material is arranged in chromosomes.

(g) Gene: This word refers to a functional portion of the genome which is responsible for the biosynthesis of a specific biological entity.

(h) Insertion: This word is used to refer to the process whereby a portion of heterologous DNA or a heterologous gene that is introduced into the genome of a host. The DNA which is inserted is referred to as an "insert".

(i) Transgene: This refers to heterologous genetic material which is transferred by insertion from the genome of one animal species to the genome of another animal species. More simply, a transgene is a gene which is heterologous to the host. The transgene encodes a specific biological material.

(j) Transgenic mammal or transgenic host: These terms are used to refer to a mammal or cell which has had a transgene inserted into its genome. As a result of this insertion, the transgenic host produces heterologous biological material that it would not normally synthesize. Heterologous entities are present or are produced by a transgenic host as a result of the insertion of foreign genetic material into the host cell genome.

(k) Primary gene product: This refers to a biological entity which is formed directly as a result of the transcription and translation of a homologous or heterologous gene. Examples thereof include proteins, antibodies, enzymes and the like.

(p) Secondary gene product: This refers to a product which is formed as a result of the biological activity of a primary gene product. An example thereof, is an oligosaccharide which is formed as a result of the catalytic activity of an enzyme.

(m) Biological products: This term is used to refer to products produced or synthesized by a transgenic host, as a result of the insertion of a transgene into the genome of the mammal. More specifically, the term means biological products which are secondary gene products. One example hereof, as described below, is human oligosaccharides produced by transgenic cows. Human oligosaccharides are produced as a result of the catalytic activity of human glycosyltransferases. As discovered herein, when the gene encoding human glycosyltransferases is inserted into the murine genome, the resultant transgenic mouse produces a heterologous human glycosyltransferase as the primary gene product. The human glycosyltransferase, using homologous substrate materials, produces oligosaccharides and glycosylated proteins. The oligosaccharide, formed as a result of enzyme activity of the primary gene product, is also properly called a secondary gene product. Glycoconjugates are another example of the class of compounds referred to herein and in the claims referred as "biological products".

(n) Product: This word is used to refer to the secondary gene products of the instant invention and is used as an alternative to "biological product".

(o) Humanized milk: This refers to milk obtained from a non-human mammal which, through alteration of the host genome, is made to produce milk which more closely resembles human milk. One example of humanized milk is cow's milk containing products found in human milk but not normally found in the cow's milk. Human oligosaccharides are produced in cow's milk as a result of the insertion of the gene encoding human glycosyltransferases into the bovine genome. Humanized milk also contains proteins glycosylated with human oligosaccharides.

As noted above, there is a considerable body of literature which describes the recombinant or transgenic expression of heterologous glycosyltransferases. However, the literature does not disclose or in any other manner suggest production of. secondary gene products in the milk of non-human transgenic mammals as claimed in the instant invention. Examples of the literature are:

1) U.S. Pat. No. 5,032,519 to Paulson teaches a method for genetically engineering cells so that they produce soluble and secretable Golgi processing enzymes instead of the naturally occuring membrane-bound enzymes.

2) U.S. Pat. No. 5,047,335 to Paulson teaches the alteration by genetic engineering of the genome of Chinese Hamster Ovary Cells (CHO) so that the CHO cells produce a sialytransferase.

3) International Patent Application No. PCT/US91/08216 teaches a transgene capable of producing hetrologous recombinant proteins in the milk of transgenic bovine species. This published patent application teaches a method for obtaining the primary gene product only. This published patent application also discloses methods of producing and using the altered milk obtained from these transgenic animals.

4) International Patent Application No. PCT/US91/05917 teaches methods for intracellularly producing DNA segments by homologous recombination of smaller overlapping DNA fragments. This published patent application teaches a method for obtaining the primary gene product only.

5) International Patent Application No. PCT/GB87/00458 teaches methods of producing a peptide, said method involving incorporating a DNA sequence coding for the peptide into the gene of a mammal coding for a milk whey protein in such a way that that the DNA sequence is expressed in the mammary gland of the adult female mammal. This published patent application teaches a method for obtaining only the primary gene product, the peptide, in the milk of the transgenic mammal, and also discloses methods of producing and using the altered milk obtained from these transgenic animals.

6) International Patent Application No. PCT/GB89/01343 teaches methods for producing proteinaceous materials in transgenic animals that have genetic constructs integrated into their genomes. The construct comprises a 5'-flanking sequence from a mammalian milk protein gene and DNA coding for a heterologous protein other than a milk protein. This published patent application teaches a method for obtaining only the primary gene product, the heterologous protein, in the milk of the transgenic mammal.

7) European Patent Application No. 88301112.4 teaches methods for targetting specific genes to the mammary gland which results in the efficient synthesis and secretion of biologically important molecules into the milk of these transgenic animals. This published patent application also teaches methods of producing and using the altered milk obtained from these transgenic animals, and a method for obtaining only the primary gene product in the milk of the transgenic mammal.

8) International Patent Application No. PCT/DK93/00024 teaches methods for producing human kappa-casein in the milk of transgenic animals. The genetic construct comprises a 5'-flanking sequence from a mammalian milk protein gene, such as casein or whey acid protein, and DNA coding for human kappa casein. The DNA sequence contains at least one intron. This published patent application teaches a method for obtaining only the primary gene product, the heterologous human kappa casein, in the milk of the transgenic mammal.

9) International Patent Application No. PCT/US87/02069 teaches a method for producing mammals capable of expressing recombinant proteins in their milk.

These publications each teach, in one manner or another, a means for obtaining the primary gene product of the transgene, that gene product being the active protein or enzyme which is encoded by the transgene. This literature discloses transgenic means for obtaining glycosyltransferases in non-human milk. However, none of the aforementioned publications teaches or suggests the use of transgenic animals as a means of obtaining a desired secondary gene product which is the product of the active enzyme. More particularly, however, none of the aforementioned publications teaches or suggests or in any other manner discloses the use of transgenic human glycosyltransferases in non-human milk to produce human oligosaccharides or glycoconjugates bearing those oligosaccharides. These oligosaccharides, which are the product of active glycosyltransferases, are hereinafter referred to as the "secondary gene product". Thus, the various oligosaccharides found in human milk are formed as a direct result of the genetically regulated expression of certain specific glycosyltransferases. In this regard, oligosaccharides may be properly considered to be "secondary gene products" since they are synthesized as a result of the biochemical activity of the primary gene product, the heterologous glycosyltransferase enzymes.

Human milk contains a variety of oligosaccharides and proteins. Free, soluble oligosaccharides are not normally produced by animal cells and tissues with the exception of the highly differentiated lactating mammary glands. Oligosaccharides constitute the major portion of the total carbohydrate content of human and bovine milk. The major carbohydrate constituent of mammalian milk is the disaccharide lactose. Lactose is typically found at a concentration greater than 10 mg/ml and is synthesized by the attachment of galactose to glucose. This reaction is catalyzed by the enzyme, $\beta$-1,4 galactosyltransferase. The milk of most mammals, including cows, contains only very small quantities of a few additional oligosaccharides. In contrast, human milk contains substantial amounts of a number of additional soluble oligosaccharides that are larger than lactose. All human oligosaccharides are synthesized by the sequential addition of monosaccharides to lactose. Representative oligosaccharides found in human milk are shown in Table 1.

TABLE 1

OLIGOSACCHARIDES PRESENT IN HUMAN MILK

| Structure | Common Name | Concentration (mg/liter) |
|---|---|---|
| 1. Gal-$\beta$-1,4-Glc | Lactose | 50,000 |
| 2. Fuc-a-1,2-Gal-$\beta$-1,4-Glc | 2-fucosyllactose | 200 |
| 3. Gal-$\beta$-1,3-GlcNAc-$\beta$-1,3-Gal-$\beta$-1,4-Glc | Lacto-N-tetraose | 400 |
| 4. Gal-$\beta$-1,4-GlcNAc-$\beta$-1,3-Gal-$\beta$-1,4-Glc | Lacto-N-neotetraose | 60 |
| 5. Fuc-a-1,2-Gal-$\beta$-1,3-GlcNAc-$\beta$-1,3-Gal-$\beta$-1,4-Glc | Lacto-N-fucopentaose I | 200 |
| 6. Gal-$\beta$-1,3[Fuc-a-1,4]GlcNAc-$\beta$-1,3-Gal-$\beta$-1,4-Glc | Lacto-N-fucopentaose II | 20 |
| 7. Gal-$\beta$-1,4[Fuc-a-1,3]GlcNAc-$\beta$-1,3-Gal-$\beta$-1,4-Glc | Lacto-N-fucopentaose III | 50 |
| 8. Fuc-a-1,2-Gal-$\beta$-1,3[Fuc-a-1,4]-GlcNAc-$\beta$-1,3-Gal-$\beta$-1,4-Glc | Lacto-N-difucopentaose I | 25 |
| 9. NeuAc-a-2,6-Gal-a-1,4-Glc | 6-sialyllactose | 25 |
| 10. NeuAc-a-2,3-Gal-$\beta$-1,4-Glc | 3-sialyllactose | 10 |
| 11. NeuAc-a-2,3-Gal-$\beta$-1,3-R | Sialyltetrasaccharide a | 10 |

TABLE 1-continued

OLIGOSACCHARIDES PRESENT IN HUMAN MILK

| Structure | Common Name | Concentration (mg/liter) |
|---|---|---|
| 12. Gal-β-1,3[NeuAc-a-2,6]GlcNAc-β-1,3-R | Sialyltetrasaccharide b | 35 |
| 13. NeuAc-a-2,6-Gal-β-1,4-GlcNAc-β-1,3-R | Sialyltetrasaccharide c | 50 |
| 14. NeuAc-a-2,3-Gal-β-1,3[NeuAc-a-2,6]-GlcNAc-β-1,3-Gal-β-1,4-Glc | Disialyltetrasaccharide | 60 |
| 15. NeuAc-a-2,3-Gal-β-1,3[Fuc-a-1,4]GlcNAc-β-1,3-Gal-β-1,4-Glc | Sialyl Lacto-N-fucopentaose | 50 |

-a-: denotes an alpha glycosidic linkage
R: Gal-β-1,4-Glc

The oligosaccharides in human milk are present as a result of the activity of certain specific glycosyltransferases found in human mammary tissue. For example, the alpha 1,2 linked fucose residues in structures 2,5, and 8 are produced by a unique human fucosyltransferase and characterize a phenotype known in the field of immunohematology as "secretors". These individuals are thus characterized because they synthesize human blood group substances in their salivary and other mucus secretions where the oligosaccharides are covalently attached to various proteins.

The alpha 1,4 linked fucose residues in structures 6,8, and 15 are formed as a result of the enzymatic action of a different fucosyltransferase. These oligosaccharides represent a phenotype present in individuals characterized as having a "Lewis positive" blood type. Such individuals use this fucosyltransferase to synthesize an oligosaccharide structure which corresponds to a human blood group antigen. This oligosaccharide is also found in the saliva, and other mucus secretions, and covalently attached to lipids found on the membrane of red blood cells of "Lewis positive" individuals. Structure 5 is related to the H-antigen of the ABO blood group; structure 6 is the "Lewis a" blood group antigen; structure 8 is the "Lewis b" blood group antigen.

At least fifteen human milk proteins have been identified. Some of these proteins are generally recognized to be glycosylated, i.e. they are covalently attached to certain specific oligosaccharides. The particular oligosaccharides which are covalently attached to the protein are the same as, or similar to, the oligosaccharides described above, and their formation is the result of normal genetically regulated expression of certain specific glycosyltransferase genes. The presence of a heterologous glycosyltransferase would also affect the post-translational modification of proteins. The proteins glycosylated by a heterologous glycosyltransferase are also properly known as "secondary gene products". Both homologous as well as heterologous proteins would be modified by the glycosyltransferase in a manner different from that resulting from the activity of homologous glycosyltransferases.

It has long been known that these oligosaccharides and glycosylated proteins, promote the growth of desirable bacteria in the human intestinal tract. It is also believed that the oligosaccharides in human milk inhibit the attachment of harmful microorganisms to the mouth and throat. These human oligosaccharides and specifically glycosylated proteins are absent from, or present in markedly different amounts in, bovine milk. Further, as noted previously, bovine milk contains predominantly lactose only. Human milk contains not only lactose but also numerous other oligosaccharides. Also, the amino acid composition of human milk proteins is significantly different from the amino acid composition of the corresponding cow's milk proteins. As a consequence, infants fed infant formula which comprises cow's milk may be more susceptible to intestinal disturbances such as diarrhea, or their blood plasma amino acid ratios and levels may differ from breast fed infants. For the same reasons, elderly, immunocompromised and critically ill patients also have an urgent need for the availability of a nutritional product which biochemically closely resembles the composition of human milk.

The complicated chemistry of human milk proteins and oligosaccharides has made their large scale synthesis extremely difficult. Before they can be incorporated into commercial nutritional product, a practical method for obtaining large amounts of glycosylated human milk proteins and oligosaccharides must be devised. One potential solution to this problem is the use of transgenic animals, more particularly transgenic cows which express genes or cDNAs encoding enzymes which catalyse the formation of oligosaccharides and/or proteins glycosylated with the same human oligosaccharides. Transgenic milk-bearing domestic animals, such as rabbits, pigs, sheep, goats and cows, are herein proposed as a means of producing milk containing human oligosaccharides and proteins glycosylated with human oligosaccharides. More particularly, transgenic cows are highly suitable for the production of oligosaccharides and recombinant proteins, because a single cow can produce more than 10,000 liters of milk containing as much as 300 kilograms of protein (mainly casein) per year at a very minimal cost. Thus, transgenic cows appear to be a less costly production route than other recombinant protein production methods since investment in fermentation facilities would not be required. Also, cow mammary glands are more cost effective than cultured cells, are likely to produce continuously and since milk is collected several times a day, the time between the actual synthesis and harvest can be as short as a few hours. The cow's genetic stability is greater than microbial or cell based production systems. Also, cows are relatively easy to reproduce using artificial insemination, embryo transfer and embryo cloning techniques. Further, downstream processing of cow's milk containing human transgenic proteins may require little or no purification. Publications teaching such methods are referred to below. However, none of these publications teaches, discloses or in any other manner suggests production of secondary gene products in the milk of non-human transgenic mammals as claimed in the instant invention.

"Molecular Farming: Transgenic Animals as Bioreactors" by J. Van Brunt, Biotechnology, Volume 6, page 1149–1154, 1988, describes the alteration of the genome of various large domestic milk bearing animals yielding transgenic animals capable of producing various heterologous entities. This publication suggests methods for obtaining the primary gene product only, International Patent Application No. PCT/US91/08216 describes a transgene capable of producing heterologous recombinant proteins in the milk of transgenic bovine species. This published patent application teaches a method for obtaining the primary gene product only. This application also discloses methods of producing and Using the altered milk obtained from these transgenic animals.

International Patent Application No. PCT/GB87/00458 describes methods for producing a peptide, said method involving incorporating a DNA sequence coding for the peptide into the gene of a mammal coding for a milk whey protein in such a way that that the DNA sequence is expressed in the mammary gland of the adult female mammal. This published patent application teaches a method for obtaining only the primary gene product, the peptide, in the milk of the transgenic mammal. This application also discloses methods of producing and using the altered milk obtained from these transgenic animals.

International Patent Application No. PCT/GB89/01343 teaches methods of producing proteinaceous materials in transgenic animals that have genetic constructs integrated into their genome. The construct comprises a 5'-flanking sequence from a mammalian milk protein gene and DNA coding for a heterologous protein other than a milk protein. This published patent application teaches a method for obtaining only the primary gene product, the heterologous protein, in the milk of the transgenic mammal.

European Patent Application No. 88301112.4 describes methods for targeting specific genes to the mammary glands which results in the efficient synthesis and secretion of biologically important molecules into the milk of these transgenic animals. This published application also discloses methods of producing and using the altered milk obtained from these transgenic animals and teaches a method for obtaining only the primary gene product in the milk of the transgenic mammal.

International Patent Application No. PCT/US87/02069 teaches a method for producing mammals capable of expressing recombinant proteins in the milk of lactating animals. This patent application does not disclose or in any other manner suggest production of secondary gene products in the milk of non-human transgenic mammals as claimed in the instant invention.

While transgenic animals can be used for the production of large quantities of human proteins, they have not been used for the production of secondary gene products, such as human oligosaccharides or proteins and lipids glycosylated with certain specific oligosaccharides, or human milk proteins and lipids glycosylated with certain specific oligosaccharides. None of the aforementioned publications discloses or suggests a method for producing human oligosaccharides and glycoconjugates in non-human mammalian milk. The aforementioned publications also do not disclose or suggest a method for obtaining glycoconjugates in non-human mammalian milk wherein the glycosylation is with the desired oligosaccharides. Achieving this result requires that the genome of non-human milk-bearing mammals be altered so as to ensure that the mammary tissue which selectively expresses a desired human glycosyltransferase which would then glycosylate certain proteins with the desired oligosaccharide. This approach requires the DNA encoding the desired human glycosyltransferase be incorporated into said genome. The literature also does not disclose or suggest a method for obtaining glycosylated human proteins in non-human mammalian milk wherein the glycosylation is with the desired oligosaccharides. The literature also does not disclose or suggest a method for obtaining glycosylated human milk proteins in non-human mammalian milk wherein the glycosylation is with the desired oligosaccharide moieties. Achieving .this result would require that the genome of non-human milk-bearing mammals to be altered so as to ensure that its mammary tissue selectively expresses both the human glycosyltransferase as well as the desired human proteins which are then appropriately glycosylated with the desired oligosaccharides by the active human glycosyltransferase. This approach requires not only that the DNA encoding the desired glycosyltransferase be inserted into said genome but also that the DNA encoding the desired human proteins also be incorporated into said genome.

Accordingly, it is an aspect of the present invention to provide methods for detecting succesful transgenesis of fertilized oocytes prior to implantation, such that the transplanted oocytes contain the genetic constructs required to achieve the desired glycosylation and oligosaccharide production.

It is also an aspect of the present invention to provide transgenic non-human milk bearing mammalian species which are capable of producing human glycosyltransferases that are secreted extracellularly by the mammary tissue of said mammalian species.

Further, it is also an aspect of the present invention to provide transgenic non-human milk bearing mammalian species which are capable of producing human glycosyltransferases that are secreted extracellularly by the mammary tissue into the milk produced by said mammalian species.

In addition, it is an aspect of the present invention to provide transgenic non-human milk bearing mammalian species which are capable of producing glycosylated human proteins and oligosaccharides that are secreted extracellularly by the mammary tissue into the milk produced by said mammalian species.

The present invention also relates to transgenic non-human milk bearing mammalian species which are capable of producing glycosylated human milk proteins and lipids in the milk of such transgenic animals.

It is also an aspect of the present invention to provide transgenic non-human milk bearing mammalian species which are capable of producing human oligosaccharides in the milk of such transgenic animals.

The present invention also relates to food formulations containing glycosylated human proteins, lipids and oligosaccharides from such transgenic milk.

The present invention also relates to pharmaceutical, medical diagnostic and agricultural formulations containing glycosylated proteins, lipids and oligosaccharides obtained from the milk of transgenic animals.

It is also an asp the present invention to provide transgenic bovine species that are capable of producing glycosylated proteins such as glycosylated human milk proteins and lipids in their mammary glands.

It is a further aspect of the present invention to provide transgenic bovine species that are capable of producing human oligosaccharides in the milk of such transgenic cows.

The present invention also relates to food formulations containing glycosylated proteins, lipids and oligosaccharides from such transgenic bovine milk.

The present invention also relates to pharmaceutical, medical diagnostic and agricultural formulations containing glycosylated proteins, lipids and oligosaccharides obtained from the milk of transgenic cows.

DISCLOSURE OF THE INVENTION

The instant invention uses transgenes encoding a heterologous catalytic entity for producing secondary gene products in the milk of transgenic non-human mammals. More particularly the instant invention uses transgenes encoding heterologous glycosyltransferases for producing heterologous oligosaccharides and glycosylated glycoconjugates in the milk of transgenic non-human mammals.

There is disclosed milk from a transgenic non-human mammal, said milk characterized in that it contains heterologous components produced as the secondary gene products of at least one heterologous gene contained in the genome of said transgenic non-human mammal.

Also disclosed is a product produced in the milk of transgenic non-human mammals wherein the product results from the action of a catalytic entity selected from the group consisting of heterologous enzymes and heterologous antibodies, and wherein said transgenic non-human mammal contains in its genome at least one heterologous gene encoding for said catalytic entity. Examples of the aforementioned product are oliogosaccharides and glycoconjugates.

The production of transgenic milk containing human oligosaccharides and/or proteins glycosylated with certain oligosaccharides is desirable since it provides a milk matrix wherein little or no additional purification is necessary for human consumption and wherein said transgenic milk biochemically resembles human milk.

There is disclosed humanized milk wherein said milk is produced by a non-human transgenic mammal wherein the genome of the transgenic non-human mammal contains at least one heterologous gene encoding for a human catalytic entity. The catalytic entity produces oligosaccharides and glycoconjugates that are present in the milk of said transgenic non-human mammal.

Also disclosed is a method for obtaining a humanized milk, said method comprising the steps of:

(a) inserting into the genome of a non-human mammal a heterologous gene encoding the production of a human catalytic entity wherein said catalytic entity produces a secondary gene product in the milk of said non-human mammal; and (b) milking said non-human mammal.

Also disclosed is a method for obtaining a biological product from humanized milk, said method comprising the steps of:

(a) inserting into the genome of a non-human mammal a heterologous gene encoding the production of a heterologous catalytic entity wherein said catalytic entity produces a secondary gene product in the milk of said non-human mammal; and (b) milking said non-human mammal; and (c) isolating the biological product from said milk.

Also disclosed is a transgenic non-human mammal characterized in that the genome of said mammal contains at least one heterologous gene encoding for the production of heterologous catalytic entity selected from the group consisting of enzymes and antibodies, and wherein said catalytic entity produces a second heterologous product in the milk of said mammal.

Also disclosed is a transgenic cow characterized in that the genome of said cow contains at least one heterologous gene encoding for the production of a heterologous glycosyltransferase selected from the group consisting of fucosyltransferase, galactosyltransferase, glucosyltransferase, xylosyltransferase, acetylases, glucoronyltransferases, glucoronylepimerases, sialyltransferases, mannosyltransferases, sulfotransferases, β-acetylgalactosaminyltransferases and N-acetylglucosaminyltransferases, and wherein the milk of said cow contains heterologous oligosaccharides and glycoconjugates produced by said glycosyltransferase.

Representative of non-human mammals useful in the instant invention are mice, rats, rabbits, pigs, goats, sheep, horses and cows. Representative of the heterologous genes useful in the instant invention are the genes encoding human enzymes and human antibodies. (Human enzymes and human antibodies are herein and in the claims also referred to as a catalytic entity). Exemplary of human enzymes useful in the present invention are enzymes selected from the group consisting of glycosyltransferases, phosphorylases, hydroxylases, peptidases and sulfotransferases. Especially useful in the practise of the instant invention are glycosyltransferases. Illustrative of the glycosyltransferases especially useful in the practise of the instant invention are the enzymes selected from the group consisting of fucosyltransferase, galactosyltransferase, glucosyltransferase, xylosyltransferase, acetylases, glucoronyltransferases, glucoronylepimerases, sialyltransferases, mannosyltransferases, sulfotransferases, β-acetylgalactosaminyltransferases and N-acetylglucosaminyltransferases.

Exemplary of the desired heterologous secondary gene products of the instant invention are oligosaccharides and glycoconjugates. (Heterologous secondary gene products are herein and in the claims also referred to as a "biological product" or more simply as a "product"). Representative of the heterologous oliogosaccharides produced as secondary gene products are lactose, 2-fucosyl-lactose, lacto-N-tetraose, lacto-N-neotetraose, lacto-N-fucopentaose I, lacto-N-fucopentaose II, lacto-N-fucopentaose III, lacto-N-difucopentaose I, sialyllactose, 3-sialyllactose, sialyltetrasaccharide a, sialyltetrasaccharide b, sialyltetrasaccharide c, disialyltetrasaccharide and sialyl lacto-N-fucopentaose. Illustrative of heterologous glycoconjugates produced as secondary gene products disclosed herein are glycosylated homologous proteins, glycosylated heterologous proteins and glycosyl lipids. Representative of desirable glycosylated heterologous proteins according to the practise of the instant invention are proteins selected from the group of proteins consisting of human serum proteins and human milk proteins. Exemplary of human milk proteins are proteins selected from secretory immunoglobulins, lysozyme, lactoferrin, kappa-casein, alpha-lactalbumin, beta-lactalbumin, lactoperoxidase and bile salt stimulated lipase.

There is also disclosed an enteral nutritional product containing humanized milk useful in the nutritive maintenance of an animal. Also disclosed is a pharmaceutical product containing the product of the instant invention useful in the treatment of an animal. Further disclosed is a medical diagnostic containing the product of the invention useful in the diagnosis of an animal. Also disclosed are agricultural products containing the product of the invention useful in the maintenance of crops.

Also disclosed is a method for producing a transgenic non-human mammalian species capable of producing heterologous secondary gene products in the milk of said species, said method comprising the steps of:

(a) preparing a transgene, said transgene consisting of at least one expression regulation DNA sequence functional in the mammary secretory cells of said transgenic species, a secretory DNA sequence functional in the mammary secretory cells of said transgenic species and a recombinant DNA sequence encoding a recombinant heterologous catalytic entity, said secretory DNA sequence being operably linked to said recombinant DNA sequence to form a secretory-recombinant DNA sequence and said at least one expression regulation sequence being operably linked to said secretory-recombinant DNA sequence, wherein said transgene is capable of directing the expression of said secretory-recombinant DNA sequence in mammary secretory cells of said transgenic species containing said transgene to produce a recombinant heterologous catalytic entity which when expressed by said mammary secretory cells catalyses the production of secondary gene products in the milk of said transgenic species;

(b) introducing said transgene into the embryonic target cell; transplanting the transgenic embryonal target cell formed thereby or the embryo formed herefrom into a recipient female parent; and (c) identifying at least one female offspring which is capable of producing said secondary gene products in the milk of said offspring.

Also disclosed is a method useful for producing large transgenic non-human mammals such as pigs, goats, sheep, horses and cows capable of producing heterologous secondary gene products in their milk. The disclosed method comprises the steps of:

(a) preparing a transgene capable of conferring said phenotype when incorporated into the cells of said transgenic non-human mammal (b) methylating said transgene;

(c) introducing said methylated transgene into fertilized oocytes of said non-human mammal to permit integration of said transgene into the genomic DNA of said fertilized oocytes;

(d) culturing individual oocytes formed hereby to preimplantation embryos thereby replicating the genome of each of said fertilized oocytes;

(e) removing at least one cell from each of said preimplantation embryos and lysing said at least one cell to release DNA contained therein;

(f) contacting said released DNA with a restriction endonuclease capable of cleaving said methylated transgene but incapable of cleaving the unmethylated form of said transgene formed after integration into and replication of said genomic DNA; and (g) detecting which of said cells from said preimplantation embryos contain a transgene which is resistant to cleavage by said restriction endonuclease as an indication of which pre-implantation embryos have integrated said transgene.

Also disclosed, in accord with the above method, is the removal of the first hemi-embryos which are lysed and analyzed according to steps (d) through (f), said method further comprising;

(g) cloning at least one of said second hemiembryos; and (h) to form a multiplicity of transgenic embryos.

Also disclosed is the transplantation of more than one of said transgenic embryos into recipient female parents to produce a population containing at least two transgenic non-human mammals having the same genotype and transplanting the remainder of the pre-implantation embryos containing a genomically integrated transgene into a recipient female parent and identifying at least one offspring having said desirable said phenotype being the ability of producing a heterologous secondary gene product in the milk of said species said heterologous secondary gene products being selected from the group consisting of oligosaccharides and glycoconjugates.

The DNA sequence forming the transgene useful in the present invention comprises at least three functional parts:

(a) A portion encoding the human glycosyltransferase. This portion of the transgene is hereinafter referred to as the "recombinant portion" or "recombinant sequence";

(b) A signal portion; and (c) An expression regulation portion.

The recombinant portion of the transgene comprises a DNA sequence encoding the desired glycosyltransferase enzyme. The signal portion may be naturally present or genetically engineered into the DNA sequence. This signal encodes a secretory sequence which ensures that glycosytransferase is transported to the Golgi apparatus of the cell. In the instant invention, the signal DNA sequence is functional in mammary secretory cells. These sequences are operably linked to form a expression- signal-recombinant DNA sequence. The expression sequence ensures that the transgene is expressed in certain tissue types only. In the instant invention expression is regulated to mammary secretory tissue. At least one expression regulation sequence, functional in the mammary secretory cells of the transgenic species, is operably linked to the signal-recombinant DNA sequences. The transgene so constructed is capable of directing the expression of the signal-recombinant DNA sequence in mammary secretory cells containing the transgene. Such expression results in the production of the glycosyltransferase which is secreted from the mammary secretory cells into the milk of the transgenic species.

In addition to the above described functional parts, the transgene may also comprise additional elements. For example, the recombinant portion may encode for more than one protein. Thus, in addition to encoding the glycosyltransferase it may also encode for one or more human proteins. Also multiple transgenes encoding other glycosyltransferases and other heterologous proteins may be transfected simultaneously. All additional transgenes are also operably linked to the secretory and expression regulation sequences of the glycosyltransferase transgene. Expression of multiple transgenes results not only in the production of the glycosyltransferase but also of the other proteins, all of which are secreted from the mammary secretory cells into the milk of the transgenic species.

In the presence of suitable substrate materials, the glycosyltransferase will convert individual monosaccharide units into the desired oligosaccharides. The desired oligosaccharides will be present in the milk of the transgenic species. The same glycosyltransferase enzyme will also covalently attach monosaccharides to proteins via available glycosylation sites. These proteins glycosytated with desired oligosaccharides will also be present in the milk of the transgenic species.

The advantages of the present invention will become better understood by reference to the following detailed description when taken in conjunction with the accompanying figures.

BRIEF DESCRIPTION OF THE DRAWINGS

FIG. 1 Nucleotide and amino acid sequence of human alpha 1,2-fucosyltransferase (SEQ ID NO:1);

FIG. 8 A fluorophore assisted carbohydrate electrophoresis gel following digestion of the oligosaccharide samples with a fucosidase specific for fucose-alpha-1,2-linkages.

FIGS. 1 through 10 are supplied in accord with 37 C.F.R. 1.81.

DETAILED DESCRIPTION OF THE INVENTION

Figure 2:
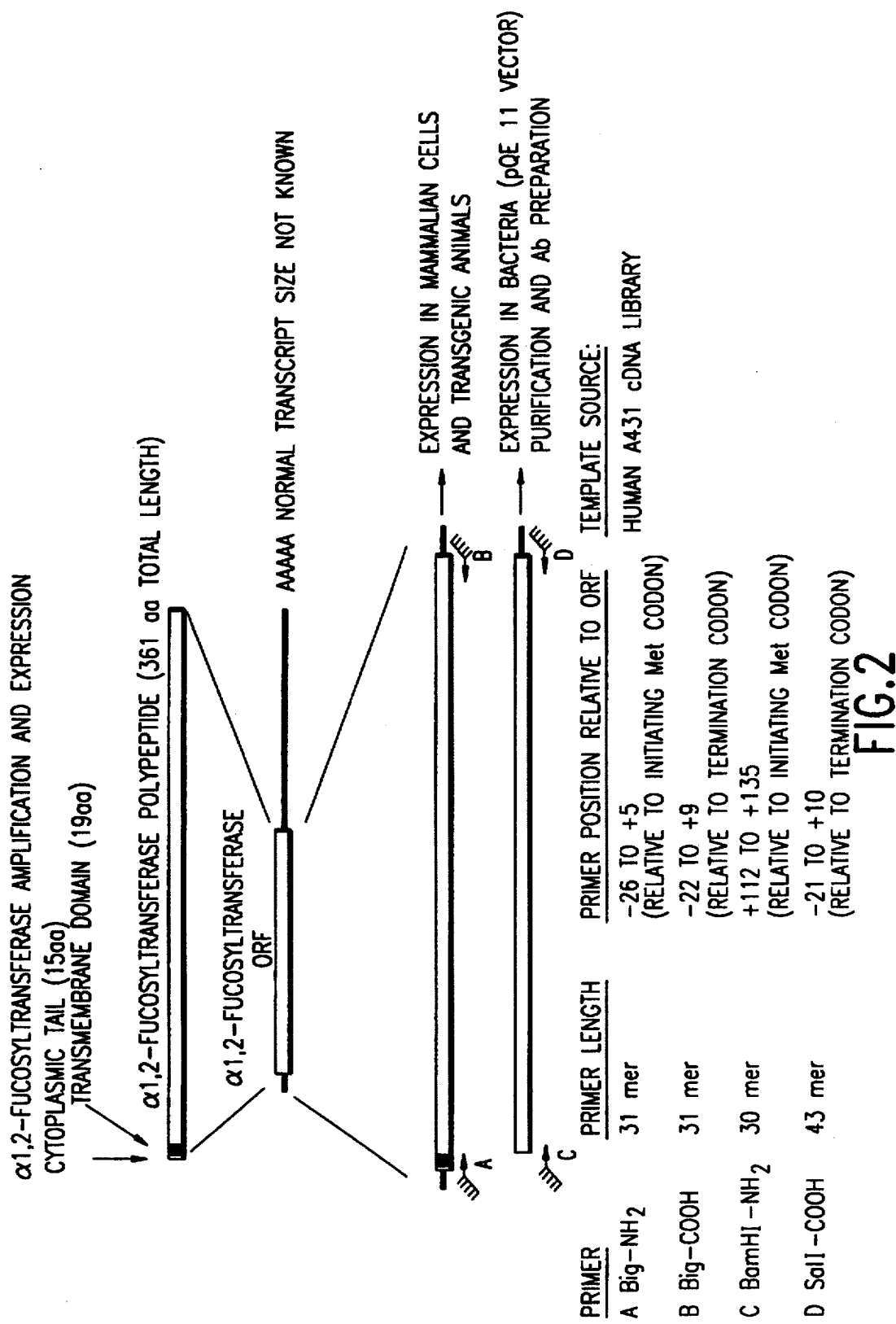
FIG. 2 Illustration of the protocol to achieve fucosyltransferase cDNA amplification and expression.

The present invention relates to the in vivo expression in mammary tissue of non-human mammals of catalytically active heterologous glycosyltransferases that control the production of secondary gene products resulting from specific. glycosyltransferase enzyme activity. These glycosyltransferase enzymes control the synthesis of free oligosaccharides or the covalent attachment of oligosaccahrides to proteins or lipids. This expression is achieved in a cell by using genetic engineering to instruct the cell to produce specific heterologous glycosyltransferases (primary gene product), and thereafter employs the specific catalytic activity associated with each glycosyltransferase to yield a specific product, the secondary gene product. In the case of glycosyltransferases, the secondary gene product includes not only the synthesized oligosaccharides but also the glycosylated proteins and lipids. The oligosaccharides and glycosylated proteins/lipids are secreted and found in free form in the milk of the transgenic mammalian species. As used herein and in the claims, the term "glycosylation" is understood to mean the post-translational modification of a protein or lipid by an enzymatic process facilitated by the expressed glycosyltransferase which results in the covalent attachment to the protein or lipid of one or more monosaccharide units. This glycosylation is accomplished by instructing the cell to produce both the glycosyltransferases as well as the protein or lipid of interest. The protein or lipid of interest may be either an homologous or heterologous entity. As used herein and in the claims, the term "homologous" is understood to refer to a composition or molecular form normally produced by the host cell or animal. As used herein and in the claims, the term "heterologous" is understood to refer to a composition or molecular form not normally produced by the host cell or animal. Genetic engineering techniques are used to incorporate into the genome of the host animal foreign genetic material, that is genetic material derived from another species. As used herein and in the claims the terms "transgenic cell" or "transgenic, animal" are understood to refer to a host cell line or an animal containing such transformed genomes. As used herein and in the claims "transgenic products" are understood to refer to products derived from such transgenic entities; for example, milk derived from a transgenic cow is referred to as transgenic milk. The present invention is based, in part, on the production of a transgenic non-human mammal in which the cells comprising the mammary gland contain a transgene which expresses a desired glycosyltransferase. (The transgenic mammary cell genome may also be transfected with a gene which encodes a human protein). The resulting glycosyltransferase, when expressed in the transgenic host mammary cell, is useful in producing soluble free oligosaccharides in the milk produced by such a transgenic animal. The expressed glycosyltransferase is also useful in the glycosylation of homologous milk proteins or heterologous human proteins when the transgenic mammary cell also expresses such proteins. The same concept can be applied to the modification of lipids.

The present invention has wide spread application to the synthesis of oligosaccharides by various glycosyltransferases such as fucosyltransferase, galactosyltransferase, glucosyltransferase, sialyltransferases, mannosyltransferases, xylosyltransferase, sulfotransferases, glucoronyltransferases, β-acetylgalactosaminyltransferase and N-acetylglucosaminyltransferases. The products of other classes of Golgi apparatus enzymes, such as acetylases, glucoronylepimerases, glycosidases, acetyltransferases, manosidases and phosphotransferases may also be synthesized by the disclosed method.

Best Mode For Carrying Out The Invention

The following describes the incorporation of the DNA encoding production of a fucosyltransferase, particularly human alpha-1,2-fucosyltransferase (hereinafter also referred to as Fuc-T), into the genome of cells forming non-human mammary glands. One example of a Fuc-T is 2'-fucosyl-lactose. This is one of the oligosaccharides in human milk and has the chemical formula, fucose-alpha-1, 2-Gal-β1,4-Glc. Other products of Fuc-T will include glycoproteins containing β-linked terminal galactose residues which can be fucosylated by Fuc-T. The resulting carbohydrate structures fucose-alpha-1,2-galactose-β-R, where R is selected from the group consisting of β-1,3-GlcNAc, β-1, 4-GlcNAc, and the like, are known in the field of blood group serology as the "H-antigen". It is well recognized by those skilled in the art that other glycosyltransferases and Golgi processing enzymes can also be used in accordance with the present invention. In the non-limiting examples described below transgenic mice were employed. The mouse genomes does not contain or express the DNA encoding Fuc-T. Thus, if transgenic mice produce either Fuc-T, 2'-fucosyl-lactose, or the H-antigen, then successful incorporation of the gene encoding Fuc-T into the murine genome must have occurred.

It is well known in the art that it is possible to insert the DNA encoding glycosyltransferases into the genome of transgenic host cells. Some of the cell lines that could be used for the transgenic expression of glycosyltransferases are Chinese Hamster Ovary (CHO) cells, mouse L cells, mouse A9 cells, baby hamster kidney cells, C-127 cells, PC8 cells, insect cells, yeast and other eukaryotic cells lines. In a preferred embodiment of the instant invention the host cells are mammary cells, said cells comprising the tissue of the mammary glands of transgenic non-human mammals. Preferred embodiments of the instant invention use transgenic mice, rats, rabbits, pigs, sheep, goats, horses or cows. Particularly preferred embodiments use transgenic sheep, goats or cows. An especially preferred embodiment of the instant invention is the use of bovine mammary tissue in transgenic lactating cows. The precise procedure used to introduce the altered genetic material into the host cell is not critical. Any of the well known procedures for introducing foreign nucleotide sequences into host cells may be used. These include use of plasmid vectors, viral vectors and any other well known methods for introducing cloned genomic DNA, cDNA, synthetic DNA or other foreign genetic material into the host cell. It is only necessary that the particular genetic engineering procedure utilized be capable of successfully introducing at least one transgene into the host cell which is then capable of expressing the desired glycosyltransferase. A preferred technique in the practice of the instant invention is the transfection of an embryonal target cell, transplanting the transgenic embryonic target cell formed thereby into a recipient surrogate parent, and identifying at least one female offspring that is capable of producing the free human oligosaccharide(s) or glycosylated human recombinant protein in its milk. A most preferred embodiment of the instant invention comprises the steps of transfection of an embryonic target cell of a bovine species, transplanting the transgenic embryonic target cell formed thereby into a recipient bovine parent and identifying at least one female bovine offspring that is capable of producing the free human oligosaccharide(s) or glycosylated homologous or heterologous recombinant protein in its milk.

The following examples demonstrate the altering of the genome of non-human mammalian host cells by inserting therein heterologous DNA that encodes for specific glycosyltransferases. The transgenic host then expresses catalytically active specific glycosyltransferases which facilitate the production of a desirable secondary gene product, more specifically a specific oligosaccharide. Glycosylation of milk proteins is also demonstrated. If, in addition to the DNA encoding for the oligosaccharides, heterologous DNA encoding for human milk proteins is also inserted into the genome of the host, then human milk proteins will also be expressed by said host. Since the same host also will express the glycosyltransferase, glycosylation of the human milk proteins with certain specific oligosaccharides will occur. Human milk proteins of interest include secretory immunoglobUlins, lysozyme, lactoferrrin, kappa-casein, lactoperoxidase, alpha-lactalbumin, β-lactalbumin and bile salt stimulated lipase.

This approach to oligosaccharide synthesis and protein/ lipid glycosylation has several advantages over other presently available methods. The approach relies on the novel combination of:

(a) the use of transgenic mammary cells for the synthesis of sugar nucleotides from natural carbon sources such as glucose;

(b) the expression of heterologous recombinant glycosyltransferase genes in transgenic mammalian cells;

(c) the production of heterologous oligosaccharides of desired structure by the natural lactating mammary glands of transgenic animals, said production being the result of the enzymatic activity of the expressed heterologous glycosyltransferase enzymes; and (d) use of the heterologous glycosyltransferase enzyme to glycosylate homologous or heterologous proteins or lipids.

The experiments described next illustrate the following points:

(a) A human alpha-1,2-fucosyltransferase gene was isolated and cloned from a human epidermal carcinoma cell line. This enzyme is responsible for the synthesis of the oligosaccharide 2'-fucosyl-lactose and for glycosylating proteins with blood group specific H-antigen;

(b) The functional nature of the gene was demonstrated by its ability to express catalytically active alpha-1,2-fucosyltransferase in cultured non-human cell lines. The presence of 1,2-fucosyltransferase was demonstrated by enzyme activity assays specific for this enzyme. The presence of catalytically active alpha-1, 2-fucosyltransferase was also demonstrated by using the technique of immunofluorescence to show the presence of the H-antigen on the surface of the cells expressing the enzyme;

(c) Utility of this gene in the formation of non-human transgenic animals capable of expressing the alpha-1, 2-fucosyltransferase gene product was demonstrated by the successful development of transgenic mice carrying the human alpha-1,2-fucosyltransferase gene which is capable of expressing catalytically active alpha-1,2-fucosyltransferase.

(d) Expression in the mammary tissue of a non-human transgenic animal of catalytically active human alpha-1,2-fucosyltransferase. The presence of the enzyme was established through direct enzyme activity assays and immunofluorescence using antibodies exhibiting binding specificity for the enzyme;

(e) Formation of secondary gene products resulting from the catalytic activity of human alpha-1,2-fucosyltransferase expressed in non-human milk. Such products include the release of the human oligosaccharide, 2'-fucosyl-lactose, into the milk and glycosylation of milk proteins with the H-antigen product of the enzyme. The presence of the secondary gene products was established through biochemical analysis of the compounds and immunofluorescence using lectins exhibiting binding specificity for the H-antigen.

The following examples are provided as representative of the scope of the invention and should not be considered limitative of the invention claimed herein.

Examples 1 and 2 utilize tissue culture systems. The vitro experiments were undertaken to prove that expression of enzymatically active heterologous glycosyltransferases was possible. Examples 1 and 2 are not critical to the enablement of the instant invention and are provided solely for the purpose of ensuring an understanding and appreciation of the invention. Examples 3, 4, 5 and 6 prove that the in vivo production of heterologous secondary gene products in the milk of transgenic non-human mammals is possible. Examples 3–6 are provided for the purpose of enablement for the teachings, scope and claims of the invention. In light of the above, Applicants believe that a biological material deposit under 37 C.F.R. §1.802 is not required.

EXAMPLE 1

Isolation of the Gene for Human Alpha-1,2-fucosyltransferase from Human Epidermal Carcinoma Cell Line The cDNA encoding alpha-1,2-fucosyltransferase was isolated from a epidermal carcinoma cell line (A 431)cDNA library, since the alpha-1,2-fucosyltransferase was previously cloned from this source (V. P. Rajan et al., J. Biological Chemistry, Volume 264, pages 11158–11167, 1989). This reference is incorporated herein by reference. After polymerase chain reaction (PCR)-mediated amplification of the protein coding sequence, the cDNA was cloned into a bacterial vector to determine the cDNA sequence of the amplified gene. The DNA sequence was determined from each of six independently isolated clones of human alpha-1,2-fucosyltransferase. This nucleotide sequence and the corresponding amino acid sequence are shown in FIG. 1

(SEQ ID NO:1). In order to determine the aforenoted cDNA sequence, two alpha-1,2-fucosyltransferase primers, each containing 31 nucleotides (31-mers), were designed based on the published alpha-1,2-fucosyltransferase cDNA sequence. Primer BigNH2 contained initiating methionine residue at position 27 where transcription of Fuc-T commences (start of open reading frame). The second primer, BigCOOH, contained a stop codon at position 10. The primers are indicated in FIG. 2. The PCR reaction included approximately 1 µM of each primer, 1 µg of template with PCR buffer and Taq polymerase. The PCR reaction was carried out in a thermal cycler (Perkin and Elmer, Model 840) using a temperature cycle of 94° C. for one minute, 60° C. for three minutes, 72° C. for three minutes for 30 cycles followed by an extension of five minutes at 72° C. The PCR reaction product was electrophoresed on a 0.8% w/v low melting point agarose. A 1.1 kilobase fragment was detected. This fragment was excised and subcloned into the PCR II cloning vector. One of the transformants, hereinafter referred to as the selectant, was selected and characterized by both restriction analysis and by nucleotide sequence analysis. DNA sequencing was performed using an Applied Biosystems Model 373A automatic DNA sequencer.

The restriction pattern of the insert indicated similarity with the coding region of alpha-1,2-fucosyltransferase. The nucleotide sequence of this candidate clone was identical to the published sequence except in position 640. In vitro site-directed mutagenesis was employed to correct this defective single base thereby forming the wild type sequence that was used in the transfection experiments described below.

EXAMPLE 2

Host Cell Expression of Human Glycosyltransferases

This example describes the transfection of cultured mouse L-cells and Chinese Hamster Ovary (CHO) cells with a gene capable of expressing the specific human glycosyltransferase, alpha 1,2-fucosyltransferase or Fuc-T. These cell lines were selected for transfection since their natural genomes do not carry the DNA encoding Fuc-T. If following transfection the cell lines are shown to produce either Fuc-T or the enzymatic products thereof (2'-fucosyl-lactose or the H-antigen attached to glycoproteins), then successful transfection will have been demonstrated. This is demonstrated by the technique of immunofluorescence using specific antibodies and/or a specific lectin which bind selectively to the H-antigen.

The Fuc-T gene used for transfection was obtained as described in Example 1. Transfection and the materials employed therein are described below.

Phenyl-β-D-galactoside was obtained from Sigma Chemical Co. The nucleotide sugar, GDP-L-(U-14C)fucose, with a specific activity of 278 mCi/mmol, was purchased from Amersham Corporation. The A431 human epidermal carcinoma cDNA library was obtained as a gift from Dr. Nevis Frigien, The University of Miami, Oxford, Ohio. PCR II vector was purchased from Invitrogen Corporation. The expression vector pQE11 was purchased from Qiagen Inc. Plasmid pSV2-neo was obtained from Pharmacia Fine Chemicals corporation. Plasmid pMet-FucT-bGH was obtained from Drs. Xhou Chen and Bruce Kelder at Ohio University, Athens, Ohio. This construct contains the cDNA which encodes Fuc-T. Primers were synthesized by Operon Technology or Fischer Scientific Corporation. Mouse monoclonal antibody to the H-antigen was purchased from the Dako Corporation. Flourescein isothiocyanate labeled goat antimouse antibodies were purchased from the Sigma Chemical Company. Rabbit polyclonal antibodies to the alpha-1,2-fucosyltransferase were raised as a means for detecting the expression of this enzyme. In order to raise enough enzyme to act as the antigen in antibody induction, the insert of the selectant was subcloned into an inducible expression vector in frame with a 6XHis tag (pQE11). A 6XHis tagged protein was easily purified with a nickel affinity chromatography column.

To avoid possible cell toxicity the hydrophobic region of the alpha-1,2-fucosyltransferase was deleted. To accomplish this, two new primers were constructed. The first, a BamHI-NH2, hybridizes to the template at position 60; the second primer, Sal I COO, spans the stop codon. The BamHI site and the Sal I were engineered onto the upstream and downstream primers. The PCR product was subcloned in frame into a BamHI/Sal I site of the pQE11 expression vector allowing fusion with the 6XHis tag. Three milligrams of the fusion protein (alpha-1,2-fucosyltransferase-6XHis) were purified using a Ni-agarose affinity column. This material was used in raising rabbit polyclonal antibodies exhibiting specificity against Fuc-T.

Cell Line and Culture

Mouse L-cells and CHO cells were obtained from the American Tissue Culture Collection (ATCC) in Washington, D.C. Cells were grown in minimum essential medium alpha (alpha-MEM, GIBCO, Grand Island, N.Y.) supplemented with 10% fetal calf serum (GIBCO), penicillin 80 u/ml (Sigma), streptomycin 80 µg/ml (Sigma) and L-glutamine (Sigma), hereinafter referred to as alpha-MEM/10% FCS. Transfected L-cells were grown on alpha-MEM containing G418 (GIBCO) at 400 µg/ml. Transfected CHO cells were grown on on alpha-MEM containing G418 (GIBCO) at 1000 µg/ml.

Transient Transfection

L-cells were grown on 8-well chamber slides (Lab-Tek) to a level of 75% confluency. A transfection cocktail was added to each chamber pMet-Fuc-bGH DNA (2 µg), lipofection (2 µl), and 200 µl Opti-MEM Medium (GIBCO). After 6 hours incubation at 37° C., 200 µl of alpha-MEM/10% FCS was added, and after 48 hours of further incubation at 37° C. the slides were processed for indirect immunofluorescence as described below.

The ability of the cloned cDNA fragment to encode functional alpha-1,2-fucosyltransferase was tested by demonstrating the presence of the catalytic product of this enzyme, i.e. the H-antigen, on the cell surface of cultured mouse L-cells. (L-cells normally do not have the H-antigen on their membrane). The wild type insert of the selectant noted in Example 1 was subcloned into plasmid pMet-bGH in an EcoR1 site. In this construct expression of alpha-1,2-fucosyltransferase activity is under the control of the met-allothionein promoter. This promoter is zinc inducible. Mouse L-cells were transiently transfected with the pMet-Fuc-bGH construct, and the presence of the H-antigen structure on the cell surface was confirmed using the technique of immunofluorescence with primary anti-H antigen mouse monoclonal antibodies as described below. The fluorescein labeled secondary antibodies were goat anti-mouse antibodies. The presence of the H-antigen was further confirmed using the fluorescein labeled lectin, Ulex europaeus agglutinin 1, that specifically binds to fucose-alpha-1,2-galactose structures.

Indirect Immunoflorescence

Successful transfection was demonstrated by the presence on the cell surface of the H-antigen. The indirect immunofluorescence assays were performed using 8-well tissue culture chamber slides. Cells were plated in each chamber at an appropriate density, incubated overnight at 37° C., and then assayed for H-antigen. The chamber slides were washed with phosphate buffered saline (PBS), fixed with 100 μl of a 2% solution of formalin in Hanks balanced salt Solution (HBSS), and permeabilizied with saponin (2 mg/ml; Sigma) in 1% of FCS, and incubated with a 1 in 1000 dilution of anti-H antibody for 60 minutes in a humid chamber at room temperature. Thereafter the slides were washed three times with PBS and incubated an additional 60 minutes with a 1:1000 dilution of FITC labeled goat anti-mouse antibody at room temperature in a humid chamber. Humidification prevented drying out of the sample.

The efficiency of L-cell transfection, or the percent of transformed L-cells which express the H-antigen, based on immunoflorescence was about 30%.

The aforenoted results clearly demonstrate the successful transfection of non-human mammalian cell lines with the DNA encoding Fuc-T. The transfected cultured cell lines produce not only the primary gene product, Fuc-T, but also modified glycoproteins. As a result of Fuc-T activity, the modified proteins bear the H-antigen. These results prove that the cloned cDNA fragment encoding Fuc-T is capable of expressing enzymatically active Fuc-T. Hence this cDNA was used for the production of transgenic animals as described below.

EXAMPLE 3

Transgenic non-human mammal possessing the gene encoding a specific human glycosyltransferase This experiment proves that transgenic non-human mammals are capable of producing a catalytically active heterologous glycosyltransferase. More specifically, transgenic animals production of human alpha-1,2-fucosyltransferase is proven. Transgenic mice were produced by microinjection of human Fuc-T cDNA into the genome of mice embryos. The fertilized mouse eggs were isolated at the single cell stage and the male pronuclei were injected with the transgenic construct containing human alpha-1,2-fucosyltransferase gene as shown in Example 1. These embryos were then implanted into pseudo-pregnant mice which had previously been mated with sterile males. Transgenic founder mice pups were identified after about 25 days after birth by using PCR amplification to analyze chromosomal DNA obtained from a fragment of the tail with probes specific for the inserted human gene. Techniques standard in the art were employed to achieve the desired transformation. Such details have been described at great length in the following references which are incorporated herein by reference and which were also discussed earlier herein:

(a) International patent Application No. PCT/US90/06874;

(b) International Patent Application No. PCT/DK93/00024;

(c) International Patent Application No. PCT/GB87/00458; and (d) International Patent Application No. PCT/GB89/01343.

Figure 3:
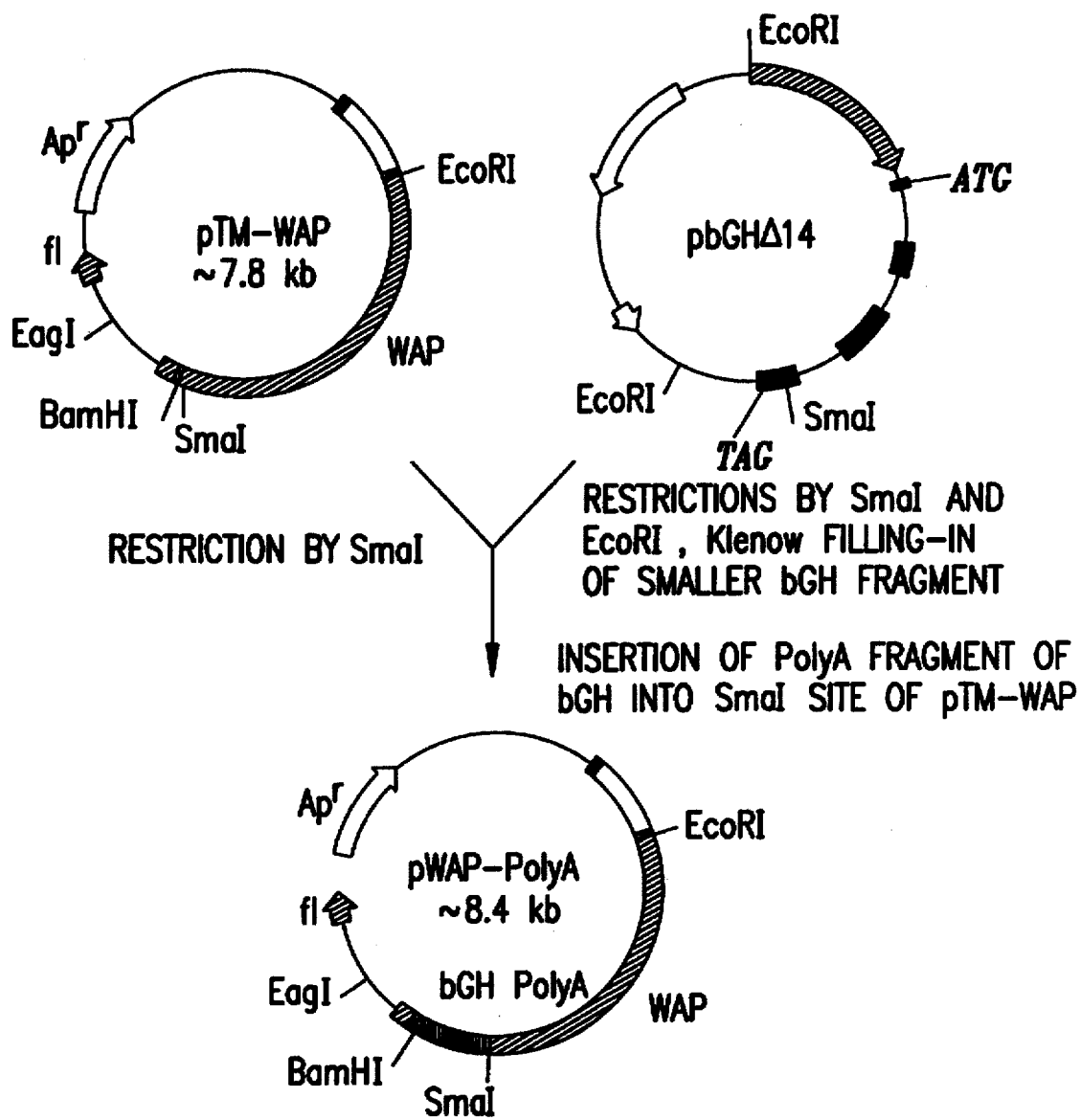
FIG. 3 Illustration of the construction of the pWAP-polyA plasmid using the regulatory sequence (promoter) of the whey acid protein (WAP).
Figure 4:
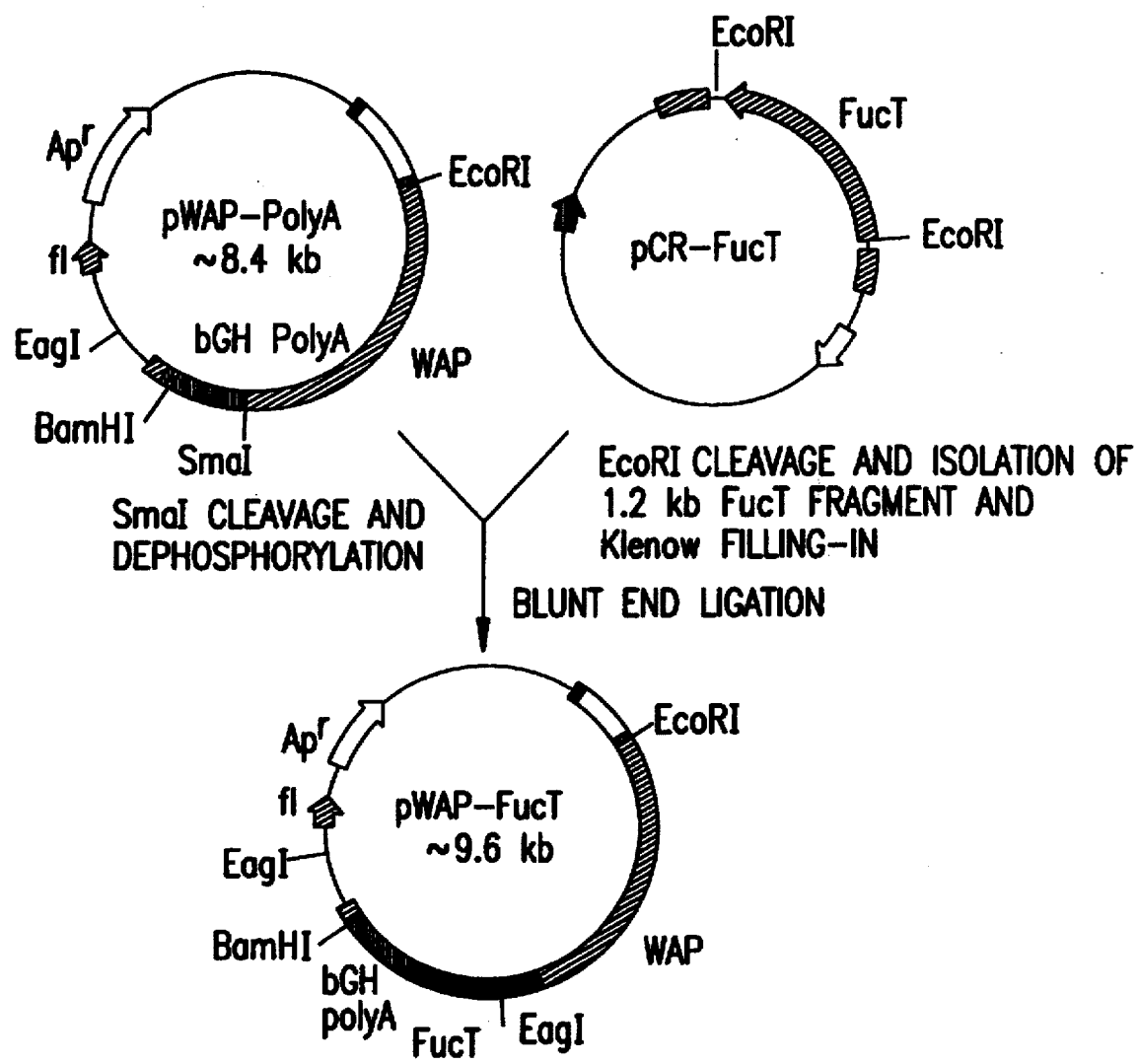
FIG. 4 Illustration of the pWAP-fucosyltransferase plasmid used for microinjection in mouse embryos.

One aspect of the present invention, relates to the expression of a catalytically active human glycosyltransferase in the milk of a non-human mammal and use of said glycosyltransferase to effect formation of the desired secondary gene product. In order to achieve mammary gland specific expression of the human gene during lactation of transgenic mice, the regulatory sequence (promoter) of the whey acidic protein (WAP) from a mouse was used to generate a transgenic construct for the expression of human alpha-1,2-fucosyltransferase. The murine WAP promoter was received as a gift from Dr. L. Henninghauser of the National Institutes of Health, Bethesda, Md. This material was used to construct the pWAP-polyA plasmid shown in FIG. 3. This plasmid contains the bovine growth hormone polyadenylation signal sequence (polyA) at the 3'-end of the fusion gene which results in effective expression, processing and stability of messenger RNA. The human alpha-1,2-fucosyltransferase (Fuc-T) gene was inserted into this plasmid to result in the formation of the pWAP-polyA-Fuc-T plasmid illustrated in FIG. 4. This plasmid was used for microinjection of the mouse embryos as described above. Using microinjections of DNA at concentrations of 2 and 4 μg/ml, a total of 85 pups were obtained from 16 injections. Only two injections did not result in pregnancy. Litter size from a single injection was normal averaging from 3 to 10 pups per litter. Tail biopsies were performed on all of 85 of the mice pups. It was determined by tail biopsy assay, that nine of the founder population, hereinafter referred to as $F_o$, possessed the gene encoding human alpha-1,2-fucosyltransferase. This corresponds to a transgenic mouse production efficiency of about 11%. This falls within the expected production efficiency range of between 5 and 25%. The $F_o$ progeny comprised eight male and one female. Six of the founders were then bred with normal mice resulting in a total of ninety-eight progeny. Thirty-eight offspring (hereinafter referred to as F1) possessed the gene encoding human alpha-1,2-fucosyltransferase as determined from tail biopsies and PCR analysis. This corresponds to a $F_1$ efficiency of about 36%. The F1 generation is comprised of nineteen males and nineteen females. Table Two summarizes the results obtained.

TABLE 2

PRODUCTION EFFICIENCY OF THE F1 GENERATION FROM SIX FOUNDER MICE

| Founder # | Total Number of Progeny | Number of Transgenic Progeny | | Efficiency Transgenesis (%) |
|---|---|---|---|---|
| | | Male | Female | |
| 6 | 16 | 4 | 2 | 37.5 |
| 28 | 18 | 2 | 2 | 22.2 |
| 29 | 18 | 4 | 6 | 55.6 |
| 34 | 13 | 3 | 6 | 69.2 |
| 54 | 15 | 2 | 1 | 20.0 |
| 72 | 18 | 4 | 2 | 33.3 |

Fifteen of the F1 (second generation) females were allowed to mature and were bred with normal mice. The pregnant F1 females were allowed to give birth. Milk was harvested from four of these F1 mothers ten days after birth. Milk collection was performed using one of two techniques that are standard in the art:

(a) mammary suction using a vaccum line connected to a trap flask and a suction cup; or (b) anesthetizing and sacrificing the animal, and then piercing the nipples to release the fluid contents of the mammary gland.

The milk samples were kept frozen on dry ice until subjected to analytical procedures as described below. The collected milk samples were prepared so as to initially separate the oligosaccharides from milk protein and lipids. This was achieved using the methods decribed by A. Kobata (Methods in Enzymology, Chapter 24, Volume 28, pages 262–271, 1972) and A. Kobata et el (Methods in Enzymology, Chapter 21, pages 211–226, 1978). The milk samples were treated as follows. The samples, typically 90–100 μl, obtained from control (non-transgenic) and trangenic animals, were centrifuged at 10,000 relative centrifugal force (RCF) for twenty minutes in conical polypropylene centrifuge tubes. Centrifugation resulted in the separation of the milk into two layers: a top layer of cream consisting of mostly lipids, and a lower layer. The lower layer, containing soluble material, was removed and transferred to a new centrifuge tube. Two equivalent volumes of ice cold ethanol were added, mixed by vortexing and centrifuged at 10,000 RCF. The ethanol soluble supernatants were recovered and concentrated by evaporation of the alcohol using a Speed-Vac concentrator. The ethanol insoluble protein pellet were kept frozen at −70° C. until further analysis. Following concentration, the oligosaccharide containing extracts were resuspended in water to the exact volume of the original milk sample. These resuspended samples were kept at 4° C. in a refrigerated autosampler until further use. When appropiate, these samples were subjected to compositional analysis as described in Examples 4 through Example 7.

One aspect of the instant invention is the transgenic expression of heterologous glycosyltransferases in the mammary gland of non-human milk-bearing mammals. The expression of heterologous glycosyltransferases can be demonstrated in two ways:

(a) directly, by determining the presence of the enzyme (primary gene product) itself; and (b) indirectly, by determining the presence of the enzyme product (secondary gene product: oligosaccharide or glycosylated protein) in the milk of the transgenic animal.

As noted earlier, the murine genome does not encode the specific alpha-1,2-fucosyltransferase responsible for the synthesis of the H-antigen. Thus, if either Fuc-T or the products of Fuc-T is present in milk of transgenic mice, then succesful transgenesis has occured providing a unique means of synthesizing and hence for obtaining secondary gene products. One important aspect of the instant invention is the production of heterologous secondary gene products in the milk of non-human animals. As noted earlier, secondary gene products may comprise not only the immediate product of the enzyme, the oligosaccharide, but also the glycosylated homologous or heterologous protein or lipids which are glycosylated through the covalent attachment of said oligosaccharide to the protein or lipid.

The harvested milk of Example 3 was analyzed for the presence of human alpha-1,2-fucosyltransferase and also for the presence of secondary gene products, specifically 2′-fucosyl-lactose and proteins glycosylated with the H-antigen. Examples 4, 5, 6 and 7 prove the production of human Fuc-T and Fuc-T products in the milk of non-human animals.

EXAMPLE 4

Analysis Proving the Production of a Specific Glycosyltransferase in the Milk of Trangenic Non-Human Mammals This example demonstrates the feasibility of obtaining human alpha 1,2-fucosyltransferase in the milk of transgenic mice. As noted above, the murine WAP promoter was employed to ensure site specific mammary gland expression of the human alpha 1,2-glycosyltransferase.

The ethanol insoluble milk protein precipitate, obtained from the mice as described above in Example 3, was resuspended in a sodium dodecyl sulfate (SDS) containing polyacrylamide gel electrophoresis (PAGE) buffer. The volume of SDS-PAGE buffer used to resuspend the protein pellet was exactly equal to that of the original volume of the milk sample. The reconstituted samples were assayed for the presence of alpha-1,2-fucosyltransferase. This presence was determined using immunoblot technology as described below. More specifically, Western Blots were employed.

Five microliter samples of the protein pellet resuspended in SDS-PAGE were electrophoresed on a 12.5% polyacrylamide gel. Electrophoresis was performed at 150 volts. Following electrophoresis, the resolved proteins were transferred to nitrocellulose membrane. Transmigration was performed for 1-hour at 100 volts using a 12.5 mM Tris-HCL buffer, pH 7.5, containing 96 mM glycine, 20% methanol and 0.01% SDS. Following transfer, the remaining unbound reactive groups on the nitrocellulose membranes were blocked by incubation in a 50 mM Tris-HCL buffer, pH 7.5, containing 0.5M NaCl and 2% gelatin, hereinafter referred to as TBS. Thereafter the membranes were washed three times in TBS containing 0.05% Tween-20.

The membranes were incubated for 18 hours in 1% gelatin/TBS containing 1:500 dilution of rabbit polyclonal antibody having specificity against alpha-1,2-fucosyltransferase. This polyclonal antibody was obtained as described in Example 2. Following rinsing with TBS-Tween, the membrane was then incubated with a solution of 1% gelatin-TBS containing goat anti-rabbit IgG previously conjugated to horse radish peroxidase. The membrane was then washed with TBS-Tween. The presence and position of the proteins on the nitrocellulose membrane were visualized by incubating the membrane in a 50 mL volume of TBS containing 0.018% hydrogen peroxide and 10 ml methanol containing 30 mg 4-chloro-napthol.

Figure 5:
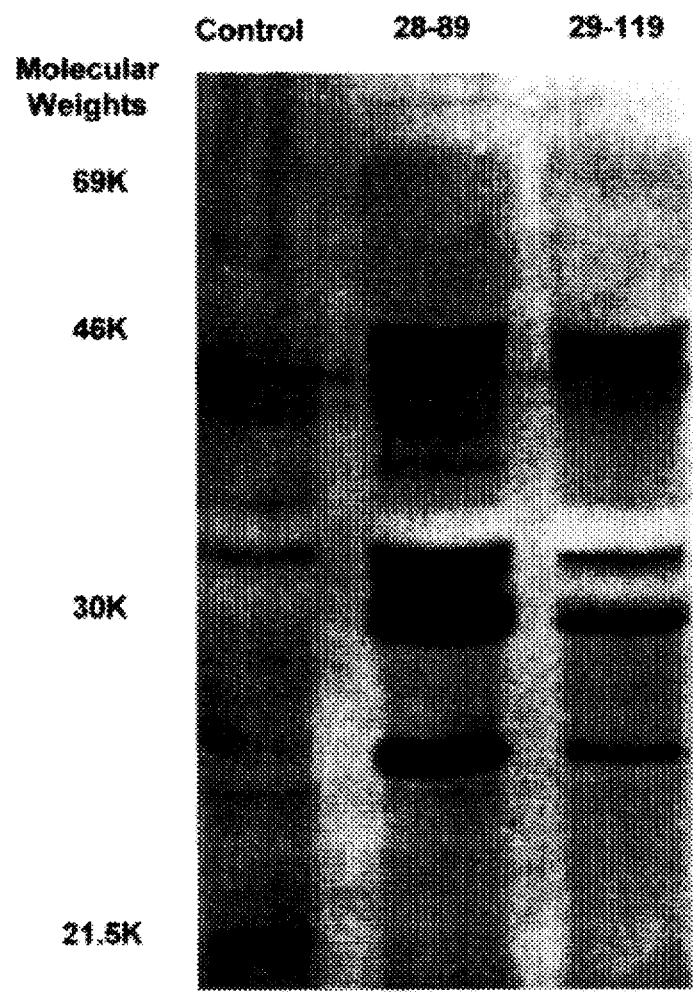
FIG. 5 A Western blot illustrating the presence of human alpha-1,2-fucosyltransferase in the milk of transgenic mice.
Figure 6A:
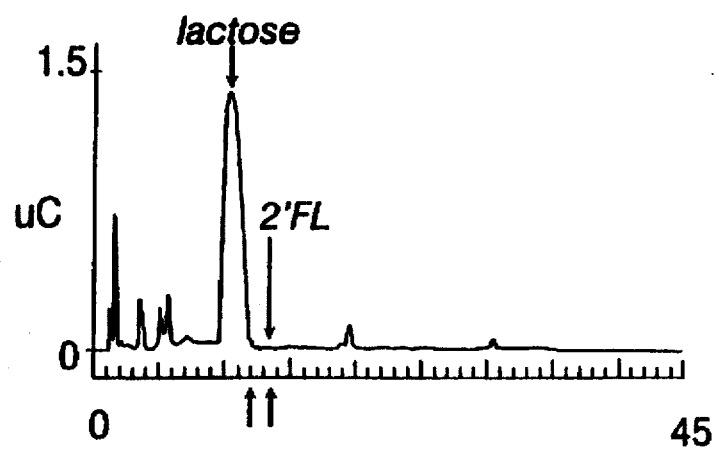
FIGS. 6A through 6F. High pressure liquid chromatography profiles of milk samples obtained from normal or non-transgenic (Frames A and B) and transgenic mice expressing human alpha-1,2-fucosyltransferase (Frames C, D, E and F).
Figure 6B:
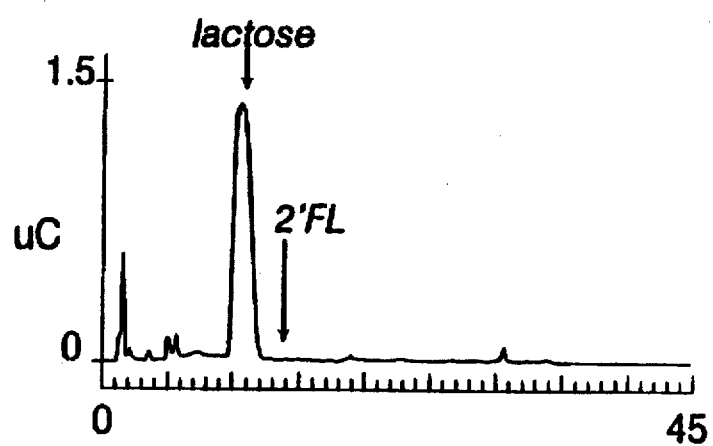
Figure 6C:
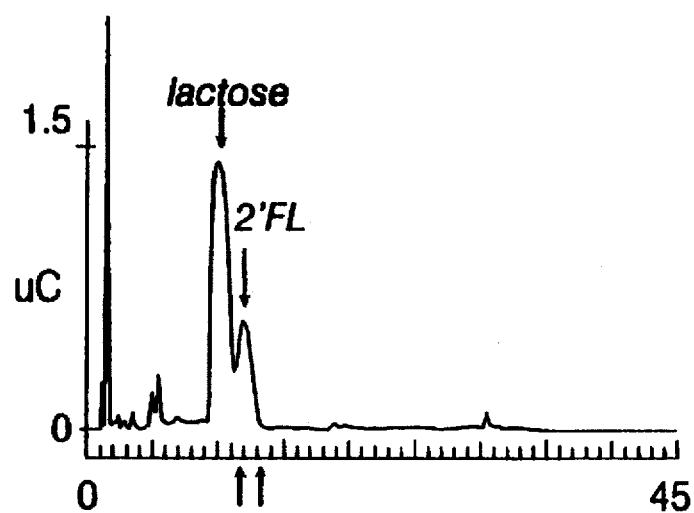
Figure 6D:
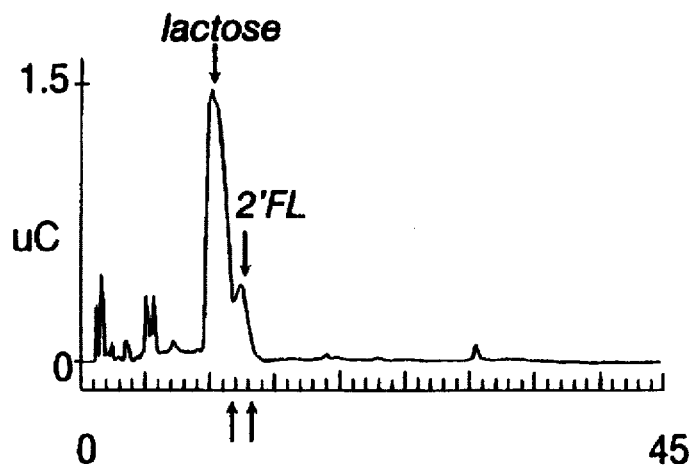
Figure 6E:
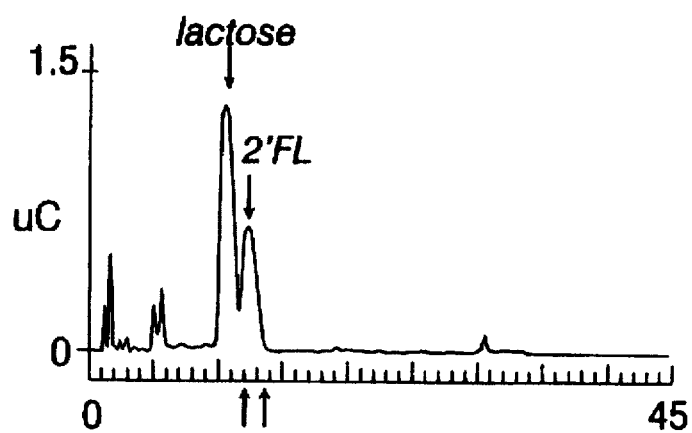
Figure 6F:
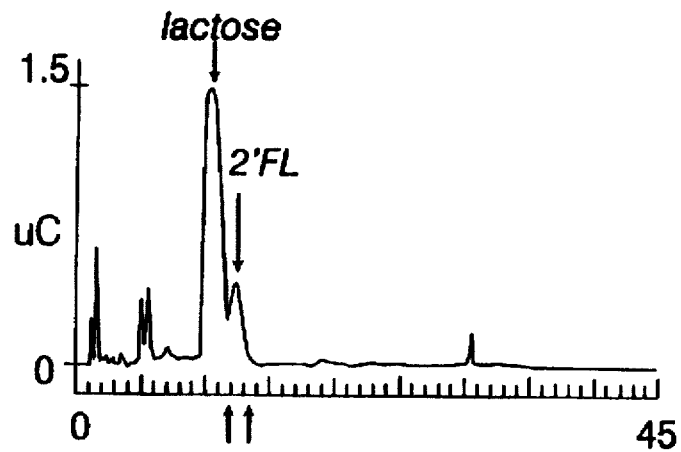

FIG. 5 shows the result of this experiment for milk samples obtained from a control (nontransgenic) and two transgenic animals. The transgenic animals are refered to in FIG. 5 as 28–89 and 29–119. The non-transgenic animals is referred to in FIG. 5 as the control. FIG. 5 indicates that a very intense band is clearly present in the milk samples obtained from the two transgenic animals but is absent from the milk obtained from the control, non-transgenic animal. Intense bands are clearly present at a relative molecular weight of approximately 46 kilodalton corresponding to the predicted molecular weight of alpha-1,2-fucosyltransferase. Intense bands are also present at positions corresponding to lower relative molecular weights in the range of about 30–25 kilodalton. These bands are absent in the milk sample derived from the non-transgenic sample. Without binding the inventors it is speculated that these lower molecular weight bands probably correspond to fragments of Fuc-T. These results prove that the milk samples from the transgenic samples contain Fuc-T whereas milk samples from the non-transgenic animal does not contain Fuc-T.

EXAMPLE 5

Analysis Proving the Production of Specific Heterologous Secondary Gene Products in the Milk of Transgenic Non-Human Mammals This example proves the feasibility of obtaining heterologous secondary gene products in the milk of non-human transgenic mammals. More specifically, this example demonstrates the ability to obtain the secondary gene product of Fuc-T in the milk of a non-human animal. Most specifically, the presence of the secondary gene product, 2'-fucosyl-lactose, in transgenic milk was demonstrated. The control non-transgenic mouse milk does not contain 2'-fucosyl-lactose.

The evaporated oligosaccharide extracts, obtained as described in Example 3, were analysed and separated employing a combination of high pressure liquid and ion exchange chromatography on a Dionex apparatus as described previously by Reddy and Bush (Analytical Biochemistry, Volume 198, pages 278–284, 1991) and Townsend and Hardy (Glycobiology, Volume 1, pages 139–147, 1991). These techniques are well known and standard in the art. The specifics of the experimental set-up, elution profiles and conditions for separation and analysis of the oligosaccharide extracts were as follows: The Dionex apparatus was fitted with a degasser to remove $CO_2$ from the elution buffers, an ion suppresser to eliminate ions from the column eluants and an on-line conductivity meter to assure the removal of ions by the ion suppresser. The chromatography parameters were as follows:

Run Time: 45 minutes

Peak Width: 50 seconds

Peak Threshold: 0.500

Peak Area Reject: 500

Injection Volume: 20 L

Flow Rate: 1.0 mL/min.

The elution gradient program, presented in Table 3, comprised the following three eluants:

Eluant 1: 600 mM Sodium Acetate in 100 mM Sodium Hydroxide

Eluant 2: Milli-Q NanoPure Water

Eluant 3: 200 mM Sodium Hydroxide

TABLE 3

| ELUTION GRADIENT PROGRAM | | | | |
|---|---|---|---|---|
| Time (minutes) | Flow (ml/min) | % #1 | % #2 | % #3 |
| 0.0 | 1.0 | 0 | 50 | 50 |
| 12.0 | 1.0 | 0 | 50 | 50 |
| 12.1 | 1.0 | 7 | 46 | 47 |
| 20.0 | 1.0 | 7 | 46 | 47 |
| 20.1 | 1.0 | 10 | 45 | 45 |
| 27.0 | 1.0 | 10 | 45 | 45 |
| 27.1 | 1.0 | 50 | 25 | 25 |
| 32.0 | 1.0 | 50 | 25 | 25 |
| 32.1 | 1.0 | 0 | 50 | 50 |
| 45.0 | 1.0 | 0 | 50 | 50 |
| 90.0 | 0.1 | 0 | 50 | 50 |

Eluted fractions were collected every 0.5 minutes.

The chromatographic profiles of milk samples obtained from two control mice and four transgenic animals expressing the alpha-1,2-fucosyltransferase are shown in FIGS. 6A through 6F. It was determined that 2'-fucosyl-lactose (which is the oligosaccharide product synthesized by the enzyme encoded by the transgene) elutes later than lactose. Review of the profiles revealed that only the transgenic animals produce milk containing a carbohydrate that co-elutes with the 2'-fucosyl-lactose standard.

Based on chromatographic peak areas it was possible to calculate the concentrations of 2'-fucosyl-lactose present in milk samples from transgenic animals using standard techniques. The data are summarized in Table 4.

TABLE 4

| Concentration of 2'-fucosyl-lactose in various non-human milk samples. | |
|---|---|
| Donor | 2'-fucosyl-lactose concentration (mg/L) |
| 1. Control (nontransgenic) | 0 |
| 2. Transgenic | |
| 28–29 | 711 |
| 29–119 | 468 |
| 34–34 | 686 |
| 72–66 | 338 |

This data proves, in accordance with the present invention, that a secondary gene product, namely a 2'-fucosyl-lactose, can be produced in the milk of transgenic non-human mammals. To further characterize the oligosaccharide a different method for the analysis of carbohydrates was used. Fluorophore Assisted Carbohydrate Electrophoresis (FACE) is a technology first described by P. Jackson, J. Chromatography, Volume 270, page 705–713, 1990.

The FACE technique was used to demonstrate unequivocally that the carbohydrate co-eluting with 2'-fucosyl-lactose has the same mobility as authentic 2'fucosyl-lactose standards in an electrophoresis system. This provides additional confirmation that the identity of the oligosaccharide contained in the transgenic milk sample is 2'-fucosyl-lactose.

In order to conduct FACE experiments with the putative 2'fucosyl-lactose, fractions separated during Dionex-HPLC chromatography were pooled. The fractions between the arrows (indicated on the abcissa) in FIGS. 6A through 6F were pooled from each sample. Portions of each pool (⅛) obtained from control and two transgenic mice and were labeled for 3 hours at 45° C. using 8-aminonaphtalene-2,3,6,-trisulphonic acid (ANTS) from Glyko Inc. (Novato, Calif.). Dried samples were resuspended in 5 μl of labeling reagent and 5 μl of reducing reagent solution (sodium cyanoborohydride) and incubated at 45° C. for 3 hours. The resulting labeled samples were dried and resuspended in 6 μl of deionized water. From this solution, a 2 μl aliquot was transferred to a fresh microcentrifuge tube. 2 μl of loading buffer containing glycerol were added and the mixture was then mixed vigorously. The total mixture (4 μl) was then subjected to electrophoresis into an "O-linked-oligosacchride gel" (Glyko). Electrophoresis was conducted at 20 milli amp constant current and 15° C. The profile of the migrated gel pattern thus obtained was imaged using a Millipore imaging apparatus.

Figure 7:
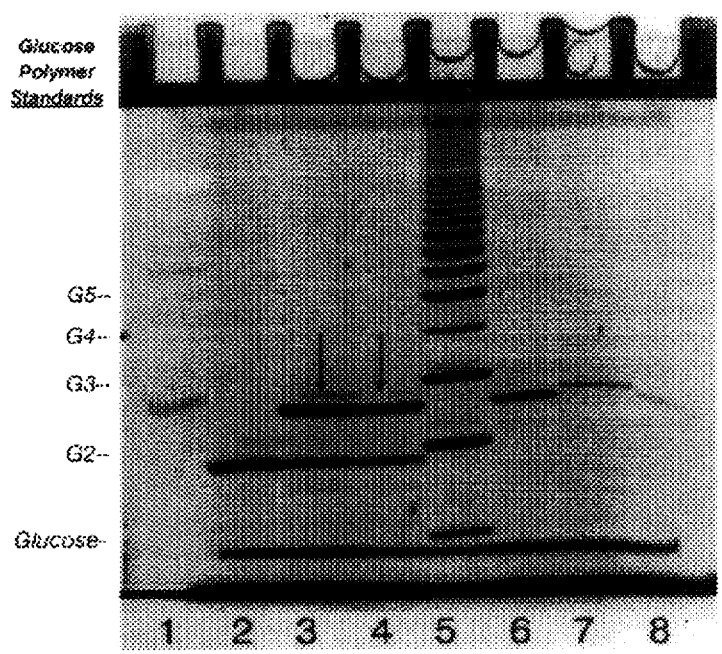
FIG. 7 A fluorophore assisted carbohydrate electrophoresis gel of oligosaccharide material pooled after high pressure liquid chromatography separation.

FIG. 7 shows the image of the gel obtained in this fashion. The sample from a control mouse (lane 2) shows a single band that migrates at the position of a lactose standard marker. The samples obtained from transgenic mice (lanes 3 and 4) contained an additional band of higher molecular weight. This band, indicated in the figure with an arrow, migrates at the position of a 2'-fucosyl-lactose standard (lane 6).

Further characterization of the oligosaccharide was performed by incubating aliquots equivalent to ⅛ of the pools illustrated in FIGS. 6A through 6F in the presence of the enzyme fucosidase which cleaves specifically at the alpha 1,2-linkages of fucose. This enzyme used was derived from Corynebacterium sp. and purchased from Panvera Corp., Madison, Wis. Dried oligosaccharides were incubated overnight in the presence of 20 μl of sodium phosphate buffer pH 6.0 containing 20 milliunits of the enzyme at 37° C. The digests were then labeled with ANTS and subjected to electrophoresis as described above.

The gels in FIG. 8 show the results from this experiment. It is readily apparent that the material that co-elutes with 2'fucosyl-lactose in Dionex-HPLC chromatography and co-migrates with the same molecule after labeling with ANTS and electrophoresis, is also susceptible to the action of the specific hydrolytic enzyme, alpha-1,2-fucosidase. 3'-fucosyl-lactose (which is the most similar isomer of 2'-fucosyl-lactose) is unaffected by the enzyme. This experiment further confirms the identity of the oligosaccharide in the transgenic milk sample as being 2'-fucosyl- lactose. In contrast, milk samples obtained from non-transgenic control animals (lane 6 and 14) following hydrolysis produce only a single band (lanes 7 and 15) migrating at the position of the galactose standard.

EXAMPLE 6

Analysis to Prove the Identity of Oligosaccharide Produced in the Milk of Transgenic Non-Human Mammals This experiment evaluated the monosaccharide units comprising the oligosaccharide. For this purpose, pooled milk samples obtained from control and transgenic mice were exhaustively treated with a mixture of glycosidases. Aliquots (⅛ of the total in 20 μl of water) from the pools illustrated in FIGS. 6A through 6F were dried by evaporation in conical tubes. The dried contents were resuspended in 20 μl of a solution containing 20 milliunits of alpha-1,2-fucosidase (Panvera, Madison, Wis.) and 20 μl of a suspension containing 30 units of *E. coli* β-galactosidase (Boehringer Mannheim, Indianapolis, Ind.). The resulting suspensions were incubated 18 hours at 37° C. under a toluene atmosphere. In this fashion, only oligosaccharides susceptible to the sequential actions of the fucosidase and the β-galactosidase were hydrolysed into their corresponding monosaccharide units.

Figure 9:
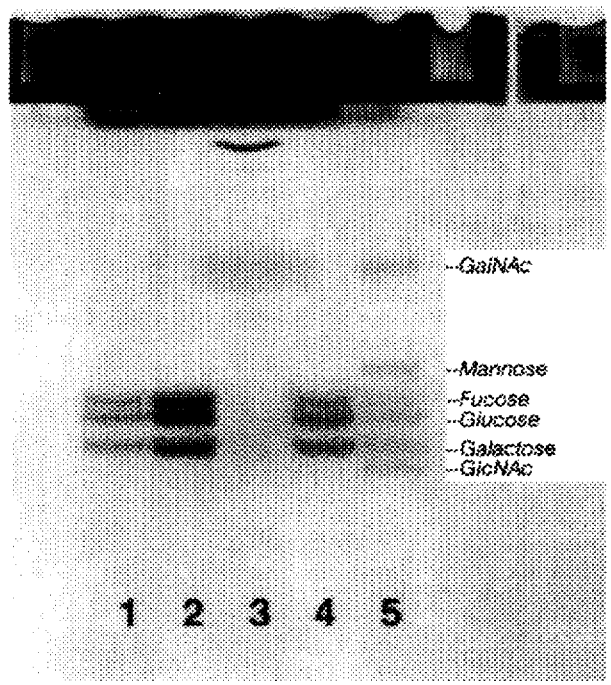
FIG. 9 A fluorophore assisted carbohydrate electrophoresis gel showing monosaccharide composition of the oligosaccharide samples isolated from milk following exhaustive digestion with a mixture of fucosidase and B-galactosidase. The released monosaccharide units were labelled with the fluorochrome 8-aminonaphtalene-2,3,6-trisulphonic acid (ANTS) to facilitate detection.

After incubation, the mixtures were dried in a Speed Vac Concentrator. The oligosaccharides resulting from this hydrolysis were labeled as described above in Example 5. Labeled monosaccharides were subjected to electrophoresis in a "Monosaccharide Gel" (Glyko). Electrophoresis was performed at 30 milliamp, constant voltage for I hour and 10 minutes. FIG. 9 shows the results from this experiment. Milk samples obtained from transgenic animals (lanes 2 and 4) contain three bands corresponding to fucose, galactose and glucose. The monosaccharides released from a 2'-fucosyl-lactose standard (lane 1) are identical to the monosaccharides released from the pools of oligosaccharides obtained from two transgenic animals (lanes 2 and 4). 3'-fucosyl-lactose is not affected by the enzymatic action of the glycosidases (lane 3). This result unequivocally establishes the identity of the oligosaccharide in the transgenic milk as being 2'-fucosyl-lactose.

Collectively, these aforediscussed results prove that the invention as described and claimed enables the production of secondary gene products in milk of transgenic animals. More specifically, the experimental data proves the feasibility of obtaining oligosaccharides in the milk of transgenic animals containing a transgene comprised, in part, of DNA encoding glycosyltransferases.

To further corroborate the invention, it was decided to demonstrate the presence of other glycoconjugates such as glycoproteins in the milk of the transgenic animals. These glycoproteins are covalent adducts of protein and oligosaccharide wherein the oligosaccharide is the product of the glycosyltransferase. The oligosaccharide is covalently attached to the protein by the glycosyltransferase.

EXAMPLE 7

Analysis Proving the Production of Glycoconjugates in the Milk of Transgenic Non-Human Mammals This example demonstrates the feasibility of obtaining glycoproteins in the milk of non-human transgenic animals. The oligosaccharide moiety is the same oligosaccharide produced as a result of the activity of the primary gene product, the glycosyltransferase. The resultant glycosylated protein is an example of a secondary gene product.

Western blots were prepared from the milk proteins of transgenic and control animals in the manner described in Example 4. However, instead of incubating the transferred membrane with polyclonal rabbit antibodies, the membrane was incubated with the lectin Ulex europaeus agglutinin I (UEA I). This lectin specifically binds to the alpha 1,2 linkage of fucose.

For this purpose, the protein pellets described in Example 3 were centrifuged at 13,000×g for 10 min., the supernatant (excess ethanol and water) was removed and the resulting pellets were resuspended in a volume of SDS-PAGE sample buffer equal to that of the original volume of milk. Five μl of these extracts were electrophoresed on 12.5% polyacrylamide SDS-PAGE as described in detail in Example 3. Following electrophoresis, the proteins were transferred to nitrocellulose membranes for 1 hour electrophoresis, the proteins were transferred to nitrocellulose membranes for 1 hour at 100 volts in 12.5 mM Tris-HCl, 96 mM glycine, 20% methanol, 0.01% SDS, pH 7.5. The nitrocellulose membranes were blocked for 1 hour with 2% gelatin in TBS(50 mM Tris-HCl pH 7.5, 0.5M NaCl) and washed 3×5 min. in TBS containing 0.05% Tween-20. The membranes were then incubated for 18 hr. in 1% gelatin/TBS containing a 1:500 dilution of peroxidase labeled-UEA-1 (Sigma, St. Louis Mo.). The resulting membrane was then washed and proteins were visualized by incubating in a mixture of 50 ml of TBS containing 0.018% hydrogen peroxide and 10 ml methanol containing 30 mg 4-chloro-naphtol (Bio Bad, Richmond, Calif.).

Figure 10:
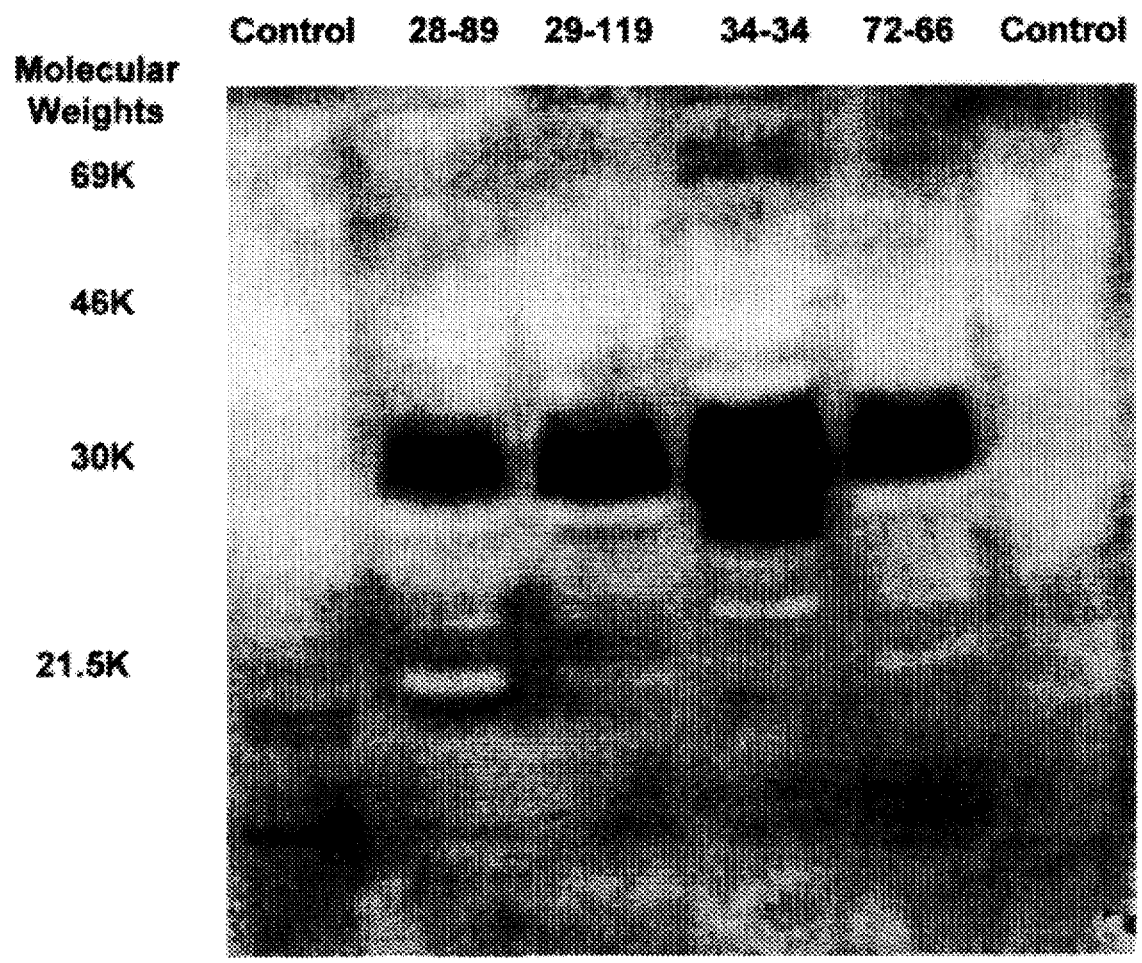
FIG. 10 A Western blot of the milk protein isolated from normal (non-transgenic) and transgenic mice expressing human alpha-1,2-fucosyltransferase. Glycosylation of the blotted proteins was detected by immunofluorescence using a lectin specific for the alpha 1,2-fucose linkage. The figure proves the presence of milk proteins glycosylated with the H-antigen product of the transgenic enzyme.

FIG. 10 shows a photograph of the visualized proteins using this technique. It is clear that only transgenic animals produced milk containing fucosylated proteins specifically recognized by the UEA-1 lectin. These proteins migrated with a relative molecular wieght of 35–40 kilodalton and are believed to be casein. These results indicate that glycoproteins bearing the 2'-fucosyl-lactose oligosaccharide (H-antigen) have been produced in the milk of transgenic animals bearing a transgene encoding alpha-1,2-fucosyltransferase. The milk of the non-transgenic control animals did not contain glycoproteins bearing 2'-fucosyl-lactose.

Examples 3–7 have proven that it is possible to produce non-human transgenic mammals capable of synthesizing secondary gene products in their milk. More specifically, it is possible to produce transgenic non-human mammals expressing human glycosyltransferases in mammary tissue resulting in the presence of human oligosaccharides and glycosylated glycoconjugates in the milk of these animals.

Industrial Applicability

The invention as described and claimed herein solves a long felt need in that it provides a means for obtaining large quantities desired oligosaccharides and glyconconjugates. The desired oligosacchrides and glycoconjugates may be isolated from the milk of the transgenic mammals and used in the preparation of pharmaceuticals, diagnostic kits, nutritional products and the like. The whole transgenic milk may also be used to formulate nutritional products that provide special advantages. The transgenic milk may also be used in the production of specialized enteral nutritional products. The invention as described and claimed avoids laborious organic chemistry and immobilized enzymatic chemistry synthesis of these very important materials that have use in pharmaceutical, research, diagnostic, nutritional, and agricultural formulas.

Having described the preferred embodiments of the present invention, it will appear obvious to those ordinarily skilled in the art that various modifications may be made to the disclosed embodiments, and that such modifications are intended to be within the scope of the present invention.

We claim:

1. A method for producing a non-human transgenic mammal whose somatic and germ cells contain a transgene, wherein expression of the transgene results in the production of oligosaccharides or glycoproteins in the milk of said mammal, the method comprising the steps of:

(a) preparing a transgene, said transgene comprising in operable association 1) at least one expression regulatory sequence functional in mammary secretory cells, 2) a DNA sequence encoding a signal sequence functional in mammary secretory cells, and 3) a DNA sequence encoding a heterologous glycosyltransferase;

(b) introducing said transgene into a non-human mammalian embryo, and transferring the resulting embryo into a recipient female; and (c) identifying at least one female offspring where expression of said transgene results in the production of a heterologous glycosyltransferase which then catalyzes the production of oligosaccharides or glycoproteins in the milk of said mammal.

2. The method according to claim 1 wherein said mammal is selected from the group consisting of mice, rats, rabbits, pigs, goats, sheep, and cows.

3. The method according to claim 1 wherein said glycosyltransferase is α-1,2-fucosyltransferase.

4. The method according to claim 1 wherein said oligosaccharides are selected from the group consisting of lactose, 2-fucosyllactose, lacto-N-tetraose, lacto-N-neotetraose, lacto-N-fucopentaose I, lacto-N-fucopentaose II, lacto-N-fucopentaose III, lacto-N-difucopentaose I, sialyllactose, 3-sialyllactose, sialyltetrasaccharide a, sialyltetrasaccharide b, sialyltetrasaccharide c, disialyltetrasaccharide and sialyl lacto-N-fucopentaose.

5. The method according to claim 1 wherein said glycoproteins are human milk proteins.

6. The method according to claim 5 wherein said human milk proteins are selected from the group consisting of secretory immunoglobulins, lysozyme, lactoferrin, kappa-casein, alpha-lactalbumin, beta-lactalbumin, lactoperoxidase and bile salt stimulated lipase.

7. A method for producing a non-human transgenic mammal whose somatic and germ cells contain a transgene, wherein expression of the transgene results in the production of oligosaccharides or glycoproteins in the milk of said mammal, the method comprising the steps of:

(a) preparing a transgene which encodes a heterologous glycosyltransferase;

(b) methylating said transgene;

(c) introducing the transgene of step (b) into fertilized eggs of a non-human mammal such that the transgene is integrated into the genome of the fertilized eggs;

(d) culturing the eggs which result from step (c) to pre-implantation embryos;

(e) removing at least one cell from each of said pre-implantation embryos, and lysing at least one cell;

(f) incubating DNA molecules released in step (e) with a restriction endonuclease which cleaves said methylated transgene but does not cleave an unmethylated form of the transgene;

(g) identifying those embryos of step (e) which contain the methylated transgene integrated into their genome;

(h) implanting at least one of the embryos identified in step (g) into a recipient female; and (i) developing to term said non-human transgenic mammal, where the expression of said transgene results in the production of oligosaccharides or glycoproteins in its milk.

8. The method according to claim 7 wherein said oligosaccharide is 2'-fucosyllactose.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
    ( A ) LENGTH:1155 base pairs
    ( B ) TYPE:Nucleic acid
    ( C ) STRANDEDNESS: Single
    ( D ) TOPOLOGY: Unknown ( i i ) MOLECULE TYPE: Cloned cDNA representing the product of a
          human genomic DNA segment.
    ( A ) DESCRIPTION: GDP-L-fucose-β-D- galactoside 2-alpha-
          fucosyl- transferase ( i i i ) HYPOTHETICAL:

( i v ) ANTI-SENSE:
    ( v ) FRAGMENT TYPE: Entire amino acid sequence provided.

( v i ) ORIGINAL SOURCE: Human Epidermal Carcinoma Cell line
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
      ( I ) ORGANELLE:

( v i i ) IMMEDIATE SOURCE: Human Epidermal Carcinoma Cell line
    ( A ) LIBRARY:
    ( B ) CLONE:

( v i i i ) POSITION IN GENOME:
    ( A ) CHROMOSOME/SEGMENT: 19
    ( B ) MAP POSITION:
    ( C ) UNITS:

( i x ) FEATURE:
    ( A ) NAME/KEY:
    ( B ) LOCATION:
    ( C ) IDENTIFICATION METHOD: DNA sequencing and restriction
          analysis
    ( D ) OTHER INFORMATION: The encoded product of nucleotide
          SEQ ID NO: 1: is the enzyme, GDP-L-fucose-'-D-
          galactoside 2-alpha-fucosyl-transferase, which has the
          amino acid sequence describe in SEQ. ID. NO: 1:. This
          enzyme is responsible for the systhesis of 2'-
          fucosyllactose.

( x ) PUBLICATION INFORMATION:
    ( A ) AUTHORS: V.P. Rajan et al
    ( B ) TITLE:
    ( C ) JOURNAL:Journal of Biological Chemistry
    ( D ) VOLUME:264
    ( E ) ISSUE:
    ( F ) PAGES:11158 - 11167
    ( G ) DATE:1989
    ( H ) DOCUMENT NUMBER:
      ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 1:

```
GAATTCGGCT TATCTGCCAC CTGCAAGCAG CTCGGCC ATG TGG CTC CGG AGC CAT    55
                                          Met Trp Leu Arg Ser His
                                           1               5

CGT CAG CTC TGC CTG GCC TTC CTG CTA GTC TGT GTC CTC TCT GTA ATC    103
Arg Gln Leu Cys Leu Ala Phe Leu Leu Val Cys Val Leu Ser Val Ile
            10                  15                  20

TTC TTC CTC CAT ATC CAT CAA GAC AGC TTT CCA CAT GGC CTA GGC CTG    151
Phe Phe Leu His Ile His Gln Asp Ser Phe Pro His Gly Leu Gly Leu
        25                  30                  35

TCG ATC CTG TGT CCA GAC CGC CGC CTG GTG ACA CCC CCA GTG GCC ATC    199
Ser Ile Leu Cys Pro Asp Arg Arg Leu Val Thr Pro Pro Val Ala Ile
        40                  45                  50

TTC TGC CTG CCG GGT ACT GCG ATG GGC CCC AAC GCC TCC TCT TCC TGT    247
Phe Cys Leu Pro Gly Thr Ala Met Gly Pro Asn Ala Ser Ser Ser Cys
55                  60                  65                  70

CCC CAG CAC CCT GCT TTC CTC TCC GGC ACC TGG ACT GTC TAC CCC AAT    295
Pro Gln His Pro Ala Ser Leu Ser Gly Thr Trp Thr Val Tyr Pro Asn
                75                  80                  85

GGC CGG TTT GGT AAT CAG ATG GGA CAG TAT GCC ACG CTG CTG GCT CTG    343
Gly Arg Phe Gly Asn Gln Met Gly Gln Tyr Ala Thr Leu Leu Ala Leu
            90                  95                 100

GCC CAG CTC AAC GGC CGC CGG GCC TTT ATC CTG CCT GCC ATG CAT GCC    391
Ala Gln Leu Asn Gly Arg Arg Ala Phe Ile Leu Pro Ala Met His Ala
            105                 110                 115

GCC CTG GCC CCG GTA TTC CGC ATC ACC CTG CCC GTG CTG GCC CCA GAA    439
Ala Leu Ala Pro Val Phe Arg Ile Thr Leu Pro Val Leu Ala Pro Glu
            120                 125                 130

GTG GAC AGC CGC ACG CCG TGG CGG GAG CTG CAG CTT CAC GAC TGG ATG    487
Val Asp Ser Arg Thr Pro Trp Arg Glu Leu Gln Leu His Asp Trp Met
135                 140                 145                 150

TCG GAG GAG TAC GCG GAC TTG AGA GAT CCT TTC CTG AAG CTC TCT GGC    535
Ser Glu Glu Tyr Ala Asp Leu Arg Asp Pro Phe Leu Lys Leu Ser Gly
                155                 160                 165

TTC CCC TGC TCT TGG ACT TTC TTC CAC CAT CTC CGG GAA CAG ATC CGC    583
Phe Pro Cys Ser Trp Thr Phe Phe His His Leu Arg Glu Gln Ile Arg
            170                 175                 180

AGA GAG TTC ACC CTG CAC GAC CAC CTT CGG GAA GAG GCG CAG AGT GTG    631
Arg Glu Phe Thr Leu His Asp His Leu Arg Glu Glu Ala Gln Ser Val
            185                 190                 195

CTG GGT CAG CTC CGC CTG GGC CGC ACA GGG GAC CGC CCG CGC ACC TTT    679
Leu Gly Gln Leu Arg Leu Gly Arg Thr Gly Asp Arg Pro Arg Thr Phe
        200                 205                 210

GTC GGC GTC CAC GTG CGC CGT GGG GAC TAT CTG CAG GTT ATG CCT CAG    727
Val Gly Val His Val Arg Arg Gly Asp Tyr Leu Gln Val Met Pro Gln
215                 220                 225                 230

CGC TGG AAG GGT GTG GTG GGC GAC AGC GCC TAC CTC CGG CAG GCC ATG    775
Arg Trp Lys Gly Val Val Gly Asp Ser Ala Tyr Leu Arg Gln Ala Met
                235                 240                 245

GAC TGG TTC CCG GCA CGG CAC GAA GCC CCC GTT TTC GTG GTC ACC AGC    823
Asp Trp Phe Pro Ala Arg His Glu Ala Pro Val Phe Val Val Thr Ser
            250                 255                 260

AAC GGC ATG GAG TGG TGT AAA GAA AAC ATC GAC ACC TCC CAG GGC GAT    871
Asn Gly Met Glu Trp Cys Lys Glu Asn Ile Asp Thr Ser Gln Gly Asp
            265                 270                 275

GTG ACG TTT GCT GGC GAT GGA CAG GAG GCT ACA CCG TGG AAA GAC TTT    919
Val Thr Phe Ala Gly Asp Gly Gln Glu Ala Thr Pro Trp Lys Asp Phe
        280                 285                 290

GCC CTG CTC ACA CAG TGC AAC CAC ACC ATT ATG ACC ATT GGC ACC TTC    967
```

```
Ala  Leu  Leu  Thr  Gln  Cys  Asn  His  Thr  Ile  Met  Thr  Ile  Gly  Thr  Phe
295            300                      305                      310

GGC  TTC  TGG  GCT  GCC  TAC  CTG  GCT  GGC  GGA  GAC  ACT  GTC  TAC  CTG  GCC   1015
Gly  Phe  Trp  Ala  Ala  Tyr  Leu  Ala  Gly  Gly  Asp  Thr  Val  Tyr  Leu  Ala
               315                      320                      325

AAC  TTC  ACC  CTG  CCA  GAC  TCT  GAG  TTC  CTG  AAG  ATC  TTT  AAG  CCG  GAG   1063
Asn  Phe  Thr  Leu  Pro  Asp  Ser  Glu  Phe  Leu  Lys  Ile  Phe  Lys  Pro  Glu
               330                      335                      340

GCG  GCC  TTC  CTG  CCC  GAG  TGG  GTG  GGC  ATT  AAT  GCA  GAC  TTG  TCT  CCA   1111
Ala  Ala  Phe  Leu  Pro  Glu  Trp  Val  Gly  Ile  Asn  Ala  Asp  Leu  Ser  Pro
          345                      350                      355

CTC  TGG  ACA  TTG  GCT  AAG  CCT  TGAGAGCCAG  GGAAGCCGAA  TTC                  1155
     360                      365
```